United States Patent
List et al.

(10) Patent No.: US 8,020,703 B2
(45) Date of Patent: Sep. 20, 2011

(54) PACKAGING SYSTEM

(75) Inventors: Hans List, Hesseneck-Kailbach (DE);
Uwe Kraemer, Ilveshiem (DE); Volker Zimmer, Laumersheim (DE); Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 262 days.

(21) Appl. No.: 12/340,241

(22) Filed: Dec. 19, 2008

(65) Prior Publication Data
US 2009/0321287 A1 Dec. 31, 2009

Related U.S. Application Data

(63) Continuation of application No. PCT/EP2007/005112, filed on Jun. 9, 2007.

(60) Provisional application No. 60/805,663, filed on Jun. 23, 2006.

(51) Int. Cl.
*B65D 69/00* (2006.01)
*B65D 83/10* (2006.01)

(52) U.S. Cl. .......... 206/572; 206/204; 206/370; 221/22; 221/45

(58) Field of Classification Search .......... 206/204, 206/225, 363, 370, 438, 570, 572, 820; 128/203.15, 128/203.21; 221/22, 25, 28, 45, 60, 70, 71, 221/73; 600/583
See application file for complete search history.

(56) References Cited

U.S. PATENT DOCUMENTS

| | | | | |
|---|---|---|---|---|
| 2,889,958 A * | 6/1959 | Ekenstam et al. | ............... | 221/25 |
| 2,989,212 A * | 6/1961 | Ekenstam et al. | ............... | 221/25 |
| 3,039,652 A * | 6/1962 | Ekenstam et al. | ............... | 221/25 |
| 3,835,992 A | 9/1974 | Adams, IV | | |
| 3,921,802 A * | 11/1975 | Thompson | ............... | 206/225 |
| 4,123,840 A | 11/1978 | Rumer, Jr. | | |
| 4,328,184 A | 5/1982 | Kondo | | |
| 5,679,311 A | 10/1997 | Harttig et al. | | |
| 5,880,829 A | 3/1999 | Kauhaniemi et al. | | |
| 6,929,004 B1 * | 8/2005 | Bonney et al. | ............. | 128/203.15 |
| 7,278,424 B1 * | 10/2007 | Davies et al. | ............. | 128/203.15 |
| 2003/0083685 A1 | 5/2003 | Freeman et al. | | |
| 2003/0211619 A1 * | 11/2003 | Olson et al. | ............... | 436/44 |
| 2004/0138688 A1 | 7/2004 | Giraud | | |
| 2004/0186394 A1 | 9/2004 | Roe et al. | | |

(Continued)

FOREIGN PATENT DOCUMENTS

DE 28 03 345 B1 6/1979

(Continued)

OTHER PUBLICATIONS

DE 198 19 407 Abstract.

(Continued)

*Primary Examiner* — Luan K Bui
(74) *Attorney, Agent, or Firm* — Woodard, Emhardt, Moriarty, McNett & Henry LLP

(57) ABSTRACT

A system comprising disposable medical devices and a packaging strip comprising a plurality of chambers containing the disposable medical devices. The strip is folded along breadthwise running fold lines to form a series of loops, each loop comprising opposing sections. The opposing sections of at least some of these loops are sealed to each other thus forming chambers between said sections. A cartridge contains such a packaging strip.

24 Claims, 20 Drawing Sheets

U.S. PATENT DOCUMENTS

| | | |
|---|---|---|
| 2005/0232815 A1 | 10/2005 | Ruhl et al. |
| 2006/0079811 A1 | 4/2006 | Roe et al. |
| 2006/0200045 A1 | 9/2006 | Roe |
| 2007/0173740 A1 | 7/2007 | Chan et al. |
| 2008/0103415 A1 | 5/2008 | Roe et al. |
| 2008/0286149 A1 | 11/2008 | Roe et al. |

FOREIGN PATENT DOCUMENTS

| | | |
|---|---|---|
| DE | 198 19 407 A1 | 11/1999 |
| DE | 198 57 426 A1 | 6/2000 |
| EP | 1 360 935 A1 | 11/2003 |
| WO | WO 02/100274 A1 | 12/2002 |
| WO | WO 2004/075760 A1 | 9/2004 |
| WO | WO 2005/107596 A2 | 11/2005 |

OTHER PUBLICATIONS

DE 198 57 426 Abstract.
DE 28 03 345 B1 Translation.
International Patent Application PCT/EP2007/005112 International Search Report mailed Feb. 21, 2008.
International Patent Application PCT/EP2007/005112 International Preliminary Report on Patentability mailed Jan. 6, 2009.

* cited by examiner

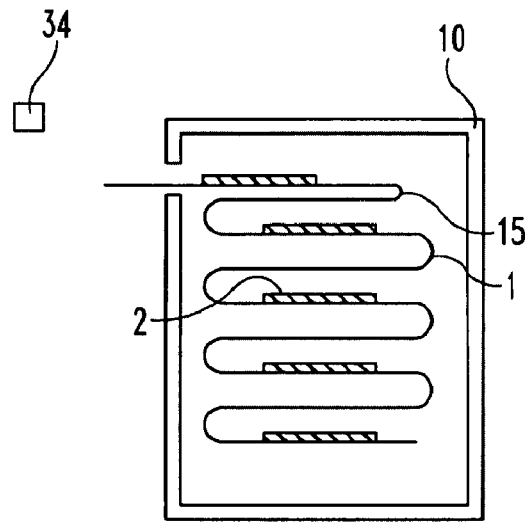
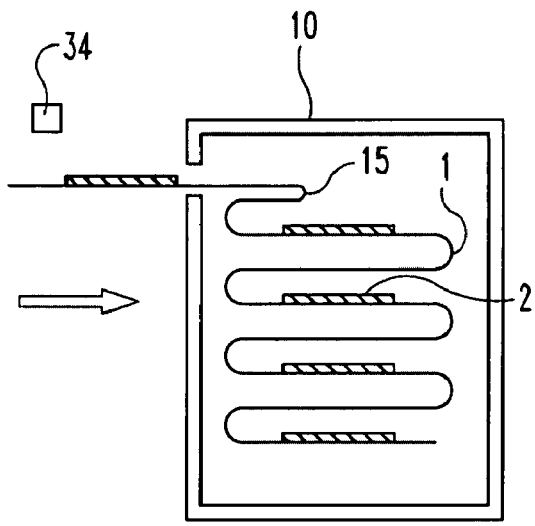
Fig. 8  Fig. 9
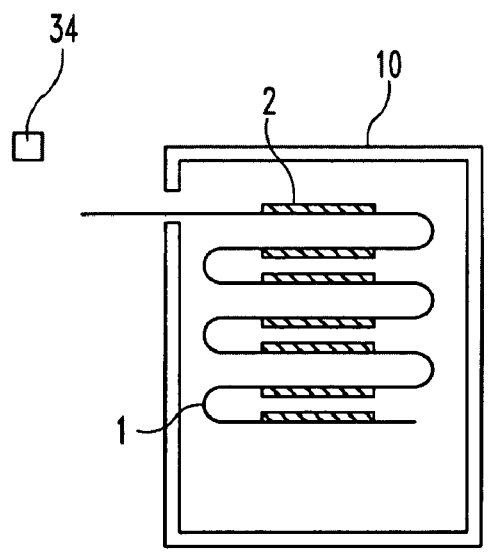
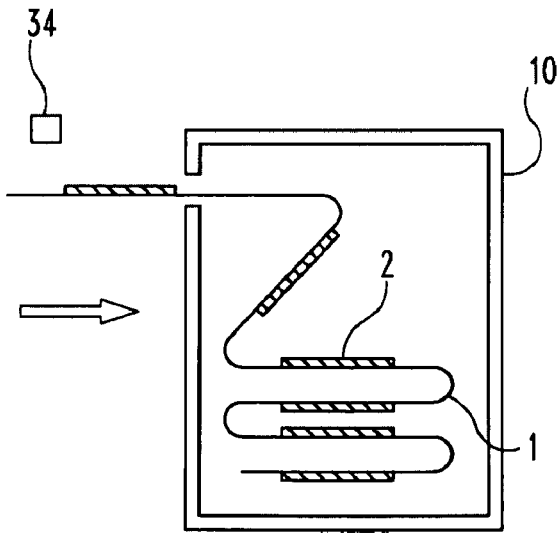
Fig. 10  Fig. 11

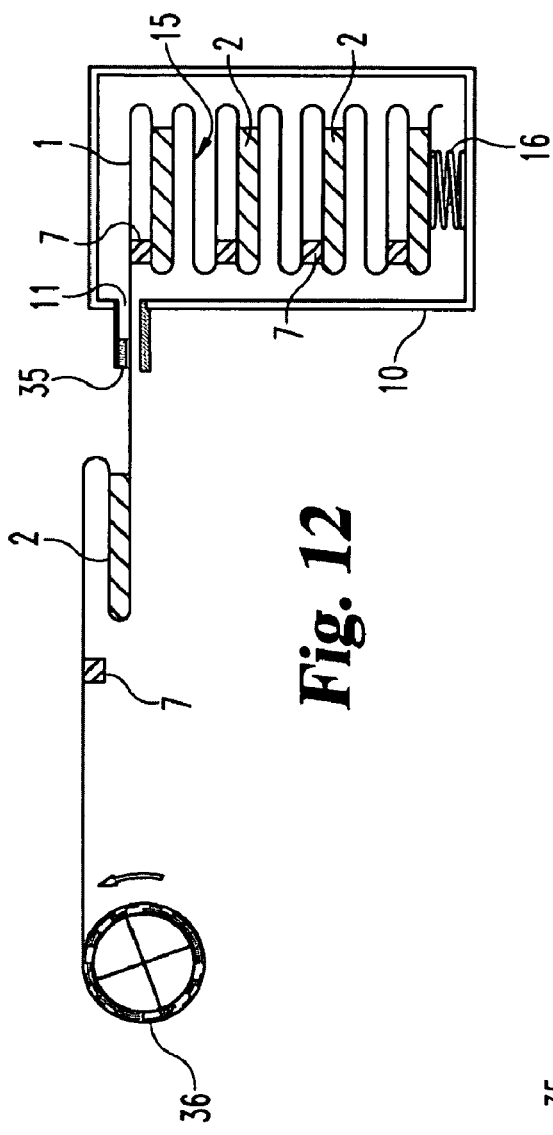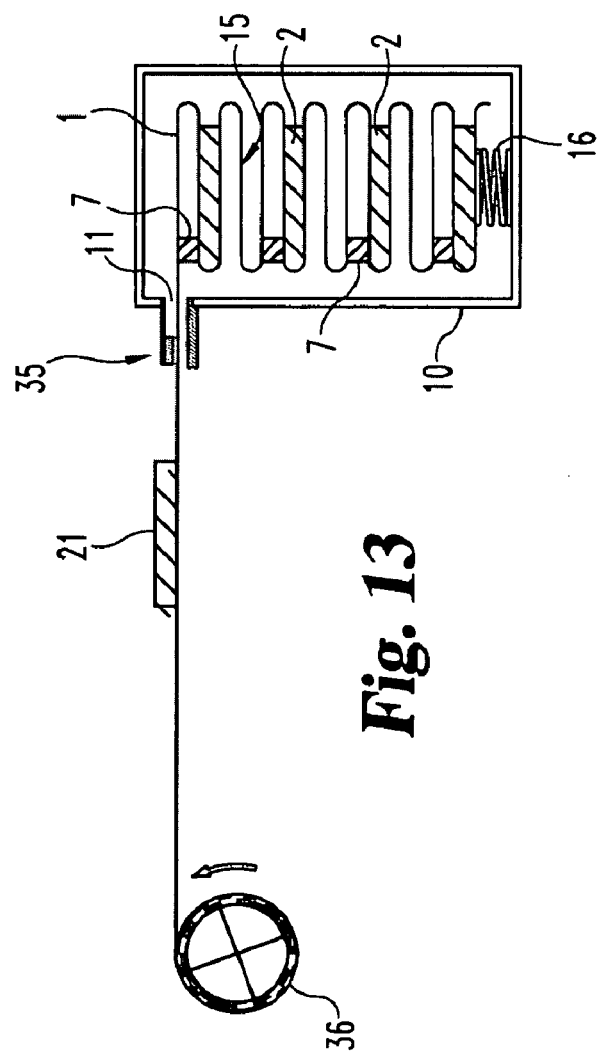

PACKAGING SYSTEM

CROSS-REFERENCE TO RELATED APPLICATION

This application is a continuation of International Application No. PCT/EP2007/005112, filed Jun. 9, 2007, which claims the benefit of U.S. Provisional Application No. 60/805,663, filed Jun. 23, 2006, both of which are hereby incorporated by reference in their entirety.

BACKGROUND

The invention relates to a packaging system comprising disposable medical devices and a packaging strip comprising a plurality of chambers containing the disposable medical devices. It is also directed to an actuation means and to cartridges to be used in the packaging system.

Disposable medical devices, like lancets and test strips for quantitative chemical analysis of fluid samples such as blood, require packaging to, for example, to protect the disposable from damage prior to use and to maintain its sterility. Furthermore, single-use disposable medical devices call for a medical device package that is inexpensive and easily disposable.

A packaging strip designed to meet these demands is known from U.S. Pat. No. 4,328,184. The known packaging strip comprises a plurality of chambers arranged on top of each other containing disposable medical devices. The strip includes a continuous base sheet and a continuous cover sheet, both sheets being of transparent polyethylene film. The base sheet and cover sheet are superposed with each other, and a plurality of disposable test elements are sandwiched there between at equal intervals. The base sheet and the cover sheet are secured together around each test element by means of heat sealing, thus forming the chambers in which the test elements are arranged.

A disadvantage of the known packaging strip is that it is rather difficult and cumbersome to unpack a disposable for use. For unpacking a disposable, it is necessary to tear off a section of the packaging strip containing a chamber with the disposable. Then the cover layer has to be peeled or torn away from the base layer. This is especially difficult for persons whose manual dexterity is impaired as is often the case with people who suffer from diabetes and/or advanced age and therefore need to use medical disposables like lancets or test elements several times a day.

Furthermore, the process of unpacking a disposable from its package in the known packaging strip is rather too complicated for use of the packaging strip in an integrated device, for example a lancing device or an analyzing device. Disposables for such automated devices are usually stored in disk or drum magazines which are loaded into the automated device and contain medical disposables. In operation such handheld devices automatically remove disposables like lancets or test elements from the magazine and use the disposable, for example, a lancet, to create a puncture wound or a test element to analyze body fluid like blood.

For stock and automatic use of lancets and test elements in medical test devices, for example for testing the glucose content of a body fluid, several prior art solutions are known. Usually the lancets are provided in a magazine module and the test elements are provided on a tape, which also may be provided in a cartridge. Both modules have to be inserted into the medical analysis device, thus resulting in a relatively integrated overall system.

It is further known to provide the lancets on the same tape as the test elements. However, in order to enable a small radius of curvature and also a small packaging volume, the lancets are fixed on the tape in a direction across to the longitudinal extension of the tape. However, in case one end of the lancet is fixed on the tape, for example for transporting and disposal purposes after having used the lance, the tape has to be moved crosswise to its longitudinal direction in the moment in which the lancet is used for piercing skin. This leads to creases in the tape and thus to a reduced reliability of the system.

SUMMARY

An object of the present invention is therefore to provide an inexpensive way for packaging disposable medical devices. Further, it should be easy to remove disposable medical devices from the inventive packaging system.

These and other objects of the invention are achieved by a packaging system comprising disposable medical devices and a packaging strip comprising a plurality of chambers containing the disposable medical devices, the strip being folded along breadthwise running fold lines, to form a series of loops, each loop comprising opposing sections, the opposing sections of at least some of these loops being sealed to each other thus forming between chambers said sections.

These objects are also achieved by a cartridge containing such a packaging system, the cartridge having a slot-shaped opening for pulling an end of the packaging strip out.

The packaging strip according to the invention can be easily manufactured using paper or plastic foil. The manufacturing costs are lower than for the known packaging strip described in U.S. Pat. No. 4,328,184, as a packaging strip according to the invention does not need a cover sheet in addition to a base sheet. According to the invention, a single sheet can be used both for forming the bottom and the top of the chambers in which the disposables are arranged.

Preferably the loops of a packaging strip according to the present invention are arranged and sealed in such a way that pulling at an end of the strip causes the loops to unfold and the chambers to open one after the other. Preferably opposing sections of the loops are sealed to each other by means of an adhesive, especially an adhesive which allows chambers to be opened by unfolding the strip, thereby peeling sealed sections apart. Suitable adhesives are used for example for adhesive labels which can be easily peeled off release paper or other smooth surfaces.

BRIEF DESCRIPTION OF THE DRAWINGS

The invention is illustrated in the following based on exemplary embodiments shown in the figures. The particularities described therein can be used separately or in combination in order to create preferred developments of the invention. In the figures:

FIG. 8 shows the cartridge of FIG. 6 before a disposable is pulled out;

FIG. 9 shows the cartridge of FIG. 8 when a disposable is pulled out;

FIG. 10 shows the cartridge of FIG. 8 with an alternative embodiment of a disposable strip before a disposable is pulled out;

FIG. 11 shows the cartridge of FIG. 10 when a disposable is pulled out;

FIG. 12 illustrates a first step when a packaging strip is pulled out of a cartridge and the steps of unfolding a loop and opening a chamber;

FIG. 13 illustrates a second step following the step of FIG. 12;

BRIEF DESCRIPTION OF SELECTED EMBODIMENTS

Figure 1:
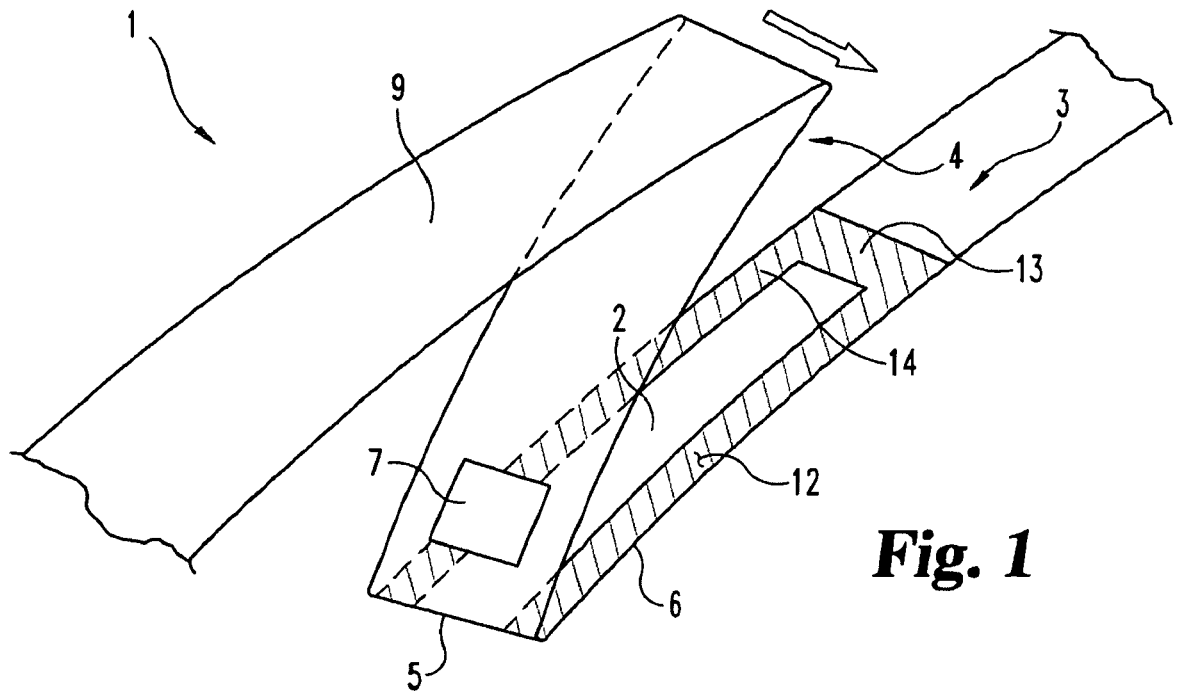
FIG. 1 shows the assembly of a packaging system according to the invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

FIG. 1 shows schematically the construction of a packaging strip 1 comprising a plurality of chambers 2. The base material of the strip can be paper, plastics, or a suitable compound material. The strip 1 is folded along breadthwise running fold lines 5 to form loops. Each loop consists of opposing sections 3 and 4. To form a chamber 2 the opposing sections 3, 4 of a loop are sealed to each other. The chambers 2 contain disposable medical devices (not shown) like lancets or chemical test elements for the analysis of body fluids and preferably a desiccant to keep the disposable medical device dry. The packaging strip 1 is also well suited for integrated disposable medical devices which comprise both a lancet and means for receiving a sample of a body fluid from a puncture wound created by piercing with the lancet, said means being for example a test element to be used in analysis.

Figure 2:
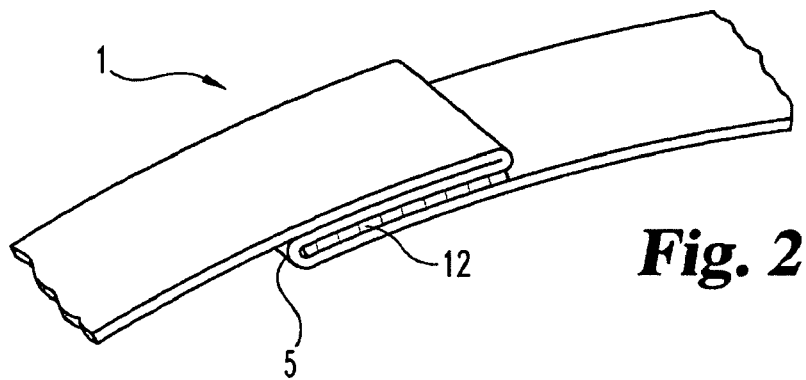
FIG. 2 shows a closed chamber of a packaging strip according to FIG. 1.
Figure 3:
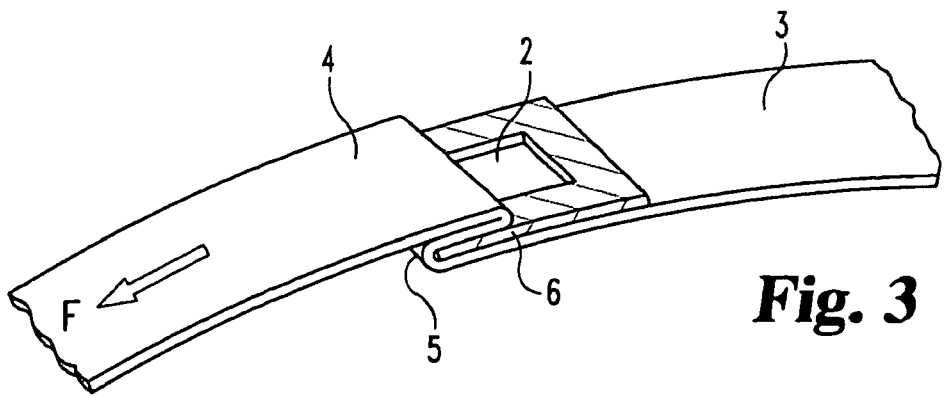
FIG. 3 shows the chamber of FIG. 2 in the process of being peeled open.

An adhesive 6 is used to seal opposing sections 3, 4 of loops to each other and thus to form the chambers 2. The adhesive 6 allows chambers 2 to be opened by unfolding the strip 1, thereby peeling opposing sections 3, 4 apart as shown in FIGS. 2 and 3. Suitable adhesives are for example known from the use of adhesive labels and release paper on which such labels are fixed before use. Preferably, the adhesive 6 forms a frame which forms sidewalls of the chamber 2, namely the three side walls 12, 13, 14. The fourth sidewall of the chamber 2 is formed by the fold line 5.

Depending on the disposables stored in the chambers 2, the thickness of the frame should be between 0.5 mm and 3.0 mm, preferably 0.8 mm and 1.5 mm. To form a suitable frame 6 the adhesive can be applied as a paste which solidifies in a suitably short time. Alternatively, a frame forming sidewalls of the chambers 2 can also be provided as a separate piece which is sealed to opposing sections 3, 4 of a loop by means of a suitable adhesive. Such a frame can, for example, be made of plastics, paper, or cardboard.

FIG. 2 shows schematically a closed chamber 2 of the packaging strip 1. FIG. 3 shows the chamber 2 of FIG. 2 in the process of being opened by peeling opposing sections 3, 4 apart. This is caused by pulling the strip 1 in the direction of arrow F. The loops of the strip 1 are arranged and sealed in such a way that when the strip 1 is subject to a tensile stress, e.g. by pulling at an end of the strip 1 wherein the other end is held fixed, the stress causes the loops to unfold and the chambers 2 to open one after the other. In principle, the following possibilities for providing the tensile stress to the strip 1 exist, which also can be combined: (i) the strip 1 is held at its back end, i.e. at the fresh folded end, and the front end, i.e. the end directed to the already used and opened chambers, is pulled in the forward direction; (ii) the front end is fixed and the back end is pulled backwards; and/or (iii) both, the front end and the back end are fixed and the strip is subjected to a displacement in a direction perpendicular to its longitudinal extension. In all cases, the chambers 2 are unfolded by the tensile stress caused due to the pulling or displacement of the strip 1.

Figure 4:
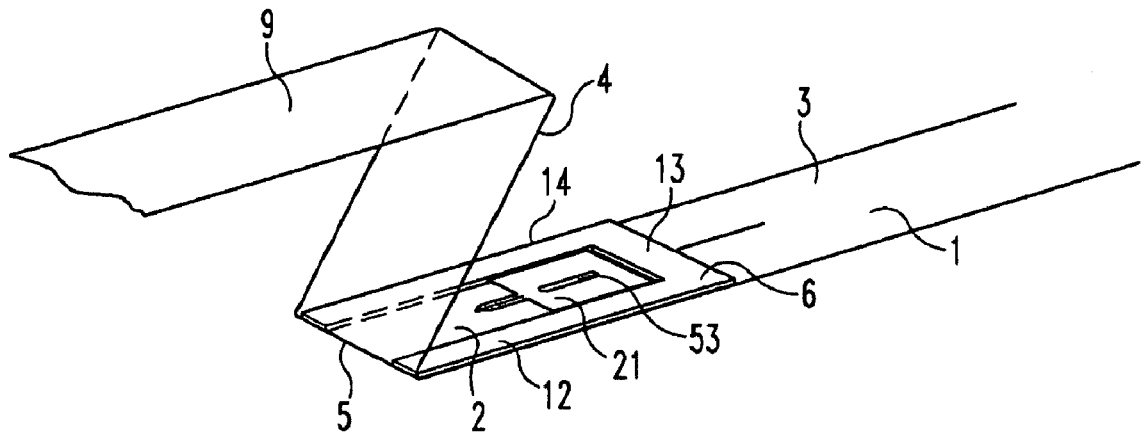
FIG. 4 shows the chamber of FIG. 1 with an inserted disposable.

FIG. 4 shows the chamber 2 of FIG. 1 with an inserted disposable which is a lancet 21. The adhesive frame 6 is u-shaped comprising the sidewalls 12, 13 and 14. The fourth, open side of that u is closed and sealed by the fold line 5 so that the chamber 2 is completely sealed.

Figure 5:
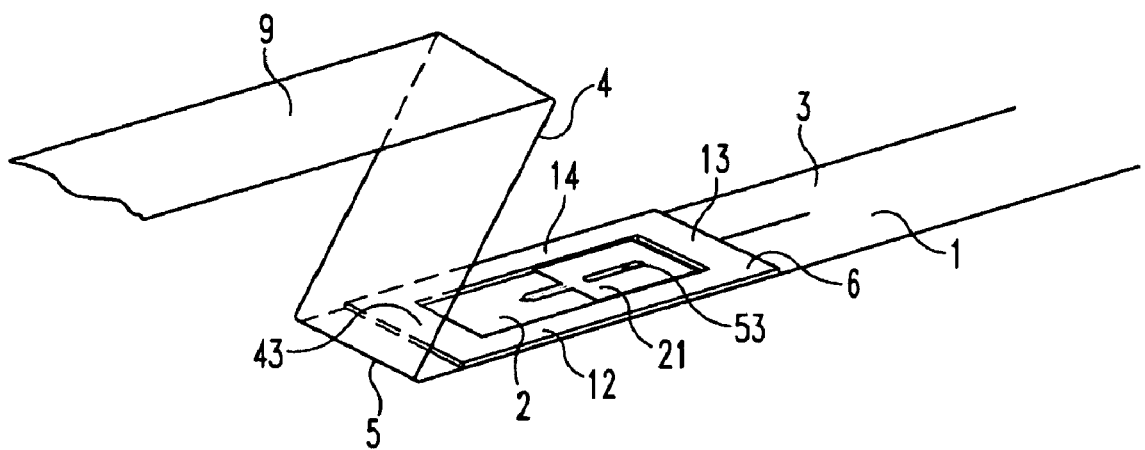
FIG. 5 shows the chamber of FIG. 1 with an alternative embodiment of an adhesive frame.

FIG. 5 shows the chamber 2 of FIG. 1 with an alternative embodiment of an adhesive frame 6 of rectangular shape comprising also a fourth sidewall 43 placed close and parallel to the fold line 5. In such embodiments the manufacturing accuracy of the strip 1 is less critical with respect to the precision of the fold line 5.

Figure 6:
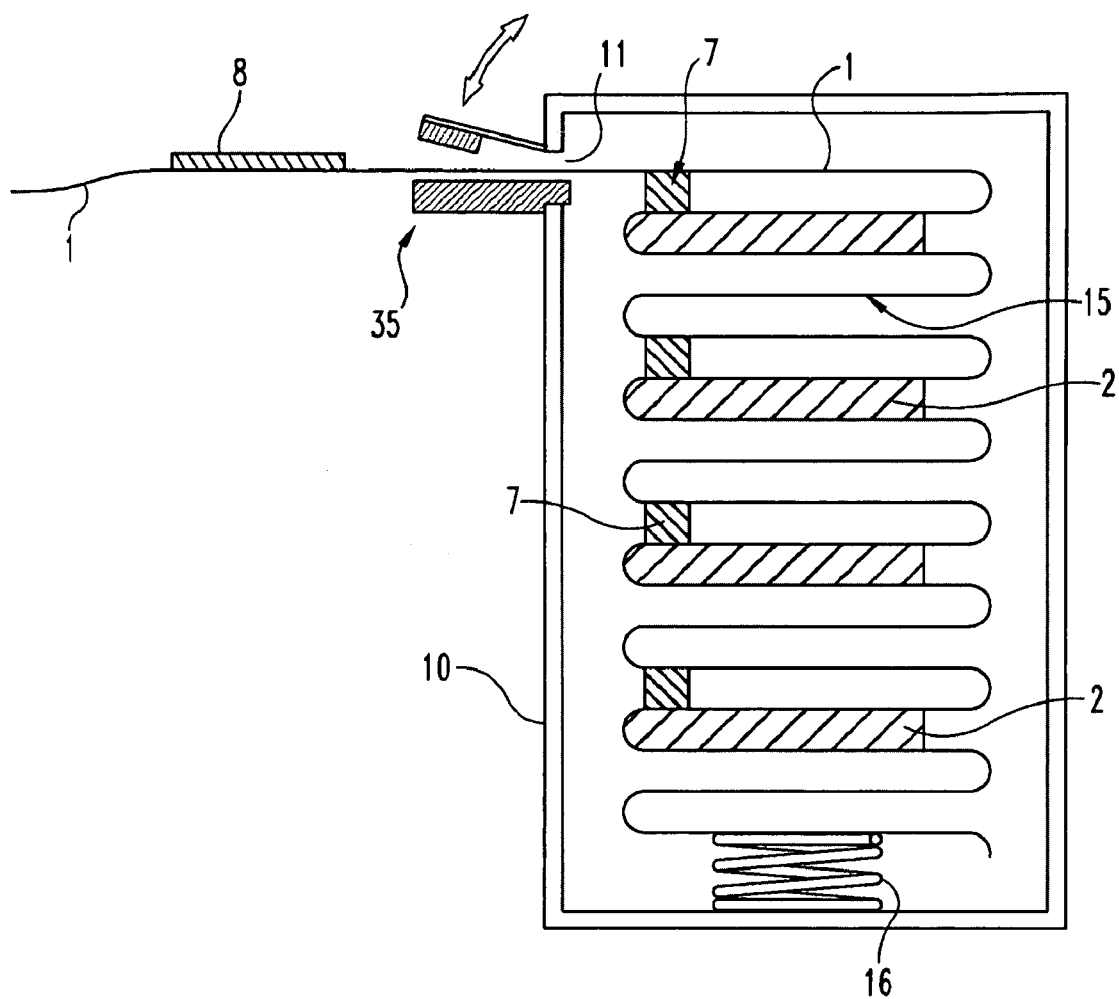
FIG. 6 shows a cartridge containing a packaging strip according to the invention.

FIG. 6 shows a cross-section of a cartridge 10 containing a packaging strip 1 as shown in FIGS. 1 to 3. The cartridge 10 has a slot-shaped opening 11 through which an end of the packaging strip 1 protrudes. Pulling the strip 1 out of the cartridge 10 automatically opens a chamber 2 as indicated in FIG. 3.

In principle it is possible to seal the opposing sections of every loop and thus to use a section of the strip 1 both as a bottom of a first chamber 2 and as a top of an adjacent chamber 2. However, it is advantageous to seal the opposing sections of only some loops, preferably only every second loop, as indicated in FIG. 6. In this way a section of the strip 1 forming a chamber bottom is arranged on top of a section of the strip 1 forming a chamber top of an adjacent chamber. In the example shown, a section of the strip 1 forms either a chamber bottom or a chamber top. Thus disposable devices 8 rest always on the same side of the strip 1 when the strip 1 is pulled out of the cartridge 10.

Preferably, disposables are fixed in the chambers 2 to the chamber bottom, i.e. the front surface of the strip 1, by means of a detachable adhesive. In this way, disposable medical devices can always be taken from precisely the same position after opening a chamber 2. This facilitates use of the packaging strip 1 in automated devices which automatically remove medical devices, particularly disposables like lancets or test elements and use them for the intended purpose. Such handheld devices for analyzing body fluids like blood or for creating puncture wounds are used, for example, by diabetics to monitor their blood glucose levels.

However, the disposables can also be permanently fixed in the chambers 2 to the chamber bottom, i.e. the front surface of the strip 1. The fixing can be performed at only a part of the disposable, e.g. a lancet 21 which may be fixed to the strip 1 with its back end only opposed to its front end intended to puncture skin in order to enable skin puncture movement of the lancet 21 together with the corresponding and attached thereto section of the strip 1. In this way the disposable, e.g. a lancet 21, can be handled and used together with the strip 1 attached thereto, wherein the strip 1 can serve as handling means for actuating the disposable fixed to the strip 1. The fixing of a disposable to the strip 1 can be realized in any suitable manner, e.g. by means of a fix adhesive, e.g. a spray adhesive or an adhesive tape, by clamping the disposable in a fold of the tape, or by riveting the disposable to the tape. If required, a tight seal should be ensured.

As FIG. 1 shows, loops forming adjacent chambers 2 are fixed to each other by a releasable adhesive, preferably an adhesive patch 7, placed between a section 4 forming a chamber bottom of a first chamber and a second section 9 forming a chamber top of a second chamber. In this way the packaging strip 1 is secured against unfolding unintentionally and a service loop (blind loop) 15 is formed between succeeding chambers 2. The stack of loops may be supported by a compression spring 16 in order to lift the top part closed to the cartridge opening 11.

Figure 7:
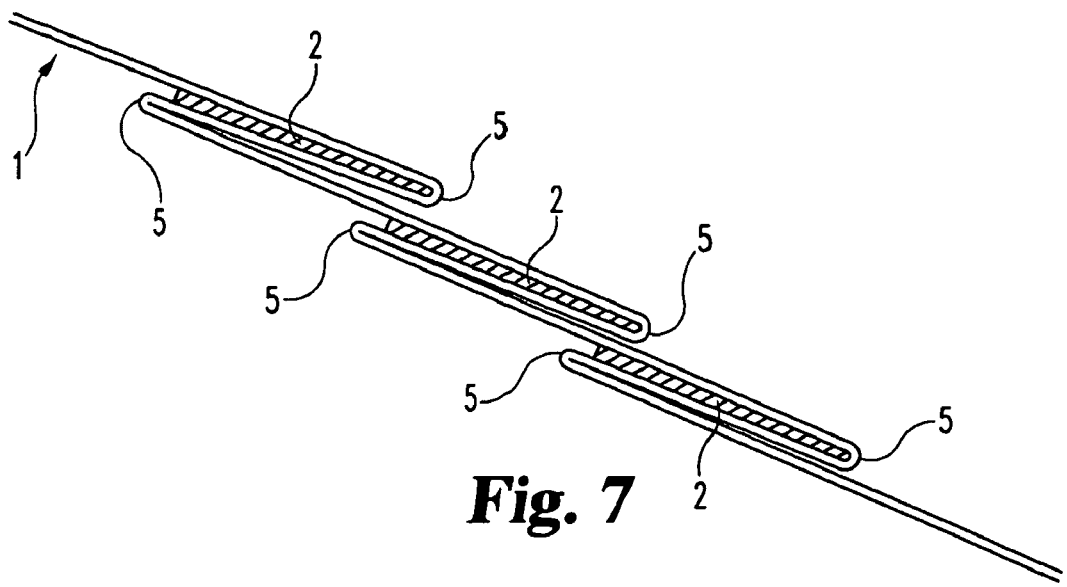
FIG. 7 shows another embodiment of a packaging strip according to the invention.

FIG. 7 illustrates an alternative embodiment in which the chambers 2 of the packaging strip 1 are not stacked "on top of each other" but are offset so that they overlap only partially (shown in the lower part of FIG. 7) or do not overlap (shown in the other part of FIG. 7). However, also in these embodiments the strip 1 is folded along breadthwise running fold lines 5 forming a series of loops, and the opposing sections of the strip are forming chambers 2 between said sections.

In order to fulfill the requirements with respect to sterility, protection against humidity, protection against other influences of the environment, but also realizing the requirements of stockage and removement of single disposables like test elements and lancets, there are two principle possibilities which can be realized with the strip 1. The first possibility is using a water-tight material or cover material of the strip 1. In this case the cartridge 10 does not have to be water-tight. The other possibility is using a non water-tight foil for the strip 1. In this case it may be preferable to use a water-tight cartridge 10 in which the strip 1 with unused disposables 8 is stored.

It has to be noted that for some embodiments of the invention, it may be preferable not to place the disposables 8 in a very closed distance, seen in the longitudinal direction of the unfolded strip 1, one after another, but to provide for a relative long distance between successive disposables 8 on the strip 1, i.e. to provide a sufficient length of the strip 1 between successive disposables 8. This may be advantageous if the disposable 8, e.g. a lancet 21, has to be actuated together with the strip 1 by an actuation means 20. The free portion of the strip 1 between successive disposables 8 can then be used for carrying out the movement of the disposable 8 without interference of another disposable 8 following too close. In practical advantageous embodiments, the distance between successive disposables 8 on the strip 1, seen in the longitudinal direction of the unfolded strip 1, i.e. the distance between subsequent chambers 2 of the strip 1 in the unfolded position of the strip 1, may be in the range from 3 cm to 20 cm, preferably from 5 cm to 10 cm.

Of course, the free portions of the strip 1 between successive disposables 8 may also be folded in additional loops, optionally using adhesive patches 7, in order to achieve a compact folding of the stack occupying only little space in the cartridge 10. In a preferred embodiment, the strip 1 may comprise in its longitudinal direction an alternating sequence of chambers 2 comprising two types of medical devices, e.g. an alternating sequence of chambers 2 comprising a lancet 21 in one chamber 2, and comprising a test element 44 in a subsequent chamber 2. This embodiment can be preferably used in glucose measuring devices, wherein the user can be provided with an alternating sequence of lancets 21 for performing a piercing movement and test elements 44 for carrying out the diabetes measuring with the blood taken by the preceding lancet 21.

A packaging strip 1 according to the invention can be produced in a preferable manufacturing process which may comprise the following steps:

1. The disposables 8, i.e. lancets 21, are placed on a longitudinal strip 1. Optionally they are fixed, e.g. by gluing.
2. The strip 1 is folded in order to form the chambers 2 comprising the lancets 21.
3. The folded strip 1 is made sterile, e.g. by applying gamma radiation.
4. The test elements 44 are placed on the strip 1 and optionally fixed to it. The test elements, for example chemical test elements, are usually sensitive and cannot be subjected to gamma radiation. Therefore, these test elements are placed after the strip 1 has been made sterile.
5. If required the test elements are also included in chambers 2 by folding the strip 1. This step is performed in case the protection against humidity requires that the test elements are comprised in a chamber 2. In case the strip 1 is packed in a humidity tight cartridge, it may not be necessary to comprise the test elements into chambers 2 by folding of the strip 1.
6. The strip 1 is cut into sections and the sections are entered into a suitable cartridge.

FIG. 8 shows a packaging system according to the invention, wherein the strip 1 comprises service loops 15 that are formed between succeeding chambers 2 in order to ensure that medical devices comprised in the chambers 2 are located on the same side of the strip 1, thus enabling an actuation means 34 handling the medical devices to take off or to handle the medical devices in an easier manner than in the case when the medical devices would be located on different, e.g. alternating, sides of the strip 1.

FIG. 9 shows how the strip 1 of FIG. 8 can be pulled out of the cartridge 10, wherein due to the service loops 15 it is not required to turn the chambers 2 within the cartridge 10. Due to this feature, the space required by the cartridge 10 can be kept smaller. Further, as can be seen by FIG. 9, it can be more easily achieved that the strip 1 remaining in the cartridge 10 when a chamber 2 is pulled out is loosened and the strip 1 within the cartridge 10 gets mixed up, although maintaining a tensile stress within the strip 1 is easier.

FIGS. 10 and 11 correspond to FIGS. 8 and 9, wherein the strip 1 does not comprise service loops 15. It can been seen that upon pulling the strip 1 out of the cartridge 10, it is required to turn the chambers 2 within the cartridge 10, thus requiring more space for the cartridge 10 in a corresponding device. In FIG. 11 it can also be seen that in this case, there is a higher chance for the strip 1 within the cartridge 10 to get mixed up.

FIGS. 12 and 13 illustrate the successive steps when a strip 1 is pulled out of a chamber 10 according to FIG. 6. The cartridge opening 11 comprises an active door 35 which can be closed to squeeze the tape 1 for fixing its position or can be opened to release the movement of the tape 1. The active door 35 provides a holding means for holding the strip 1 against the pulling direction in order to assist opening a chamber 2 of the strip 1. The tape 1 is pulled by a winding device 36 which also serves for taking up and disposing of used tape 1 with used medical devices. In FIG. 12 a chamber 2 has been pulled out of the cartridge 10 completely, the active door 35 has been closed and the strip has been pulled a little further by the winding device 36. Therefore the chamber 2 has been opened from the right to its half extension in a peeling off process by a straight and level pulling of the tape 1, wherein also the adhesive patch 7 was broken.

The opening of the chamber 2 is continued when the tape 1 is pulled further by the winding device 36 with the active door 35 staying closed until a situation according to FIG. 13 is reached in which the chamber 2 is opened fully so that the medical device, e.g. a lancet 21, is relieved from the chamber 2 and lies ready for use on top of the tape 1. It is advantageous when the strip 1, the fold lines 5, and the chambers 2 are constructed in such a manner that all medical devices lie on top of the tape 1 when the chamber 2 is opened by the peeling process. From this position the medical devices can be grasped by hand or preferably gripped by an automatic actuation means.

Figure 14:
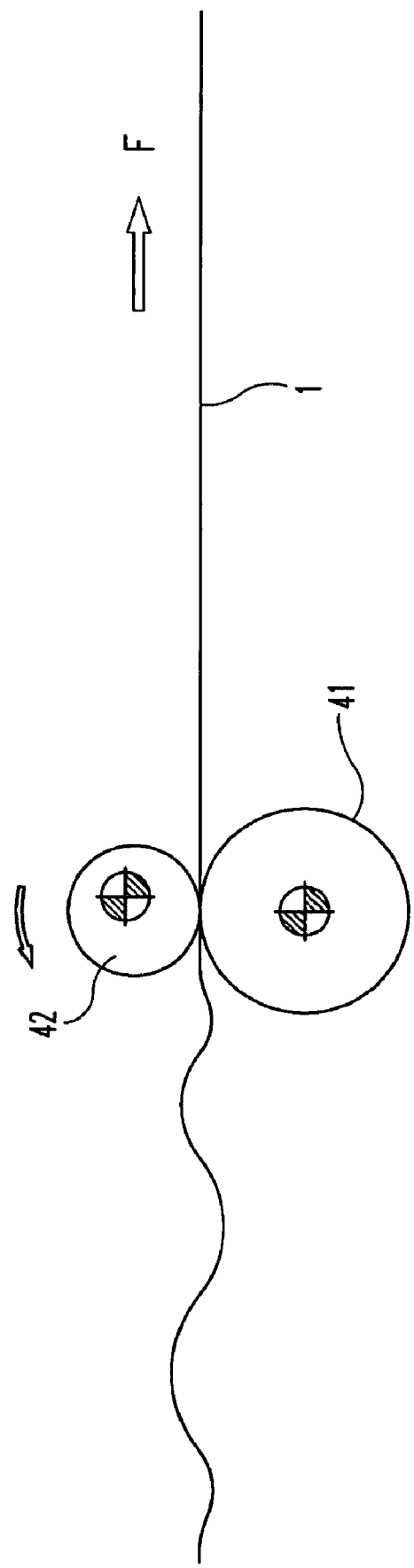
FIG. 14 illustrates a closed position of an alternative detail of FIGS. 6, 12 and 13.
Figure 15:
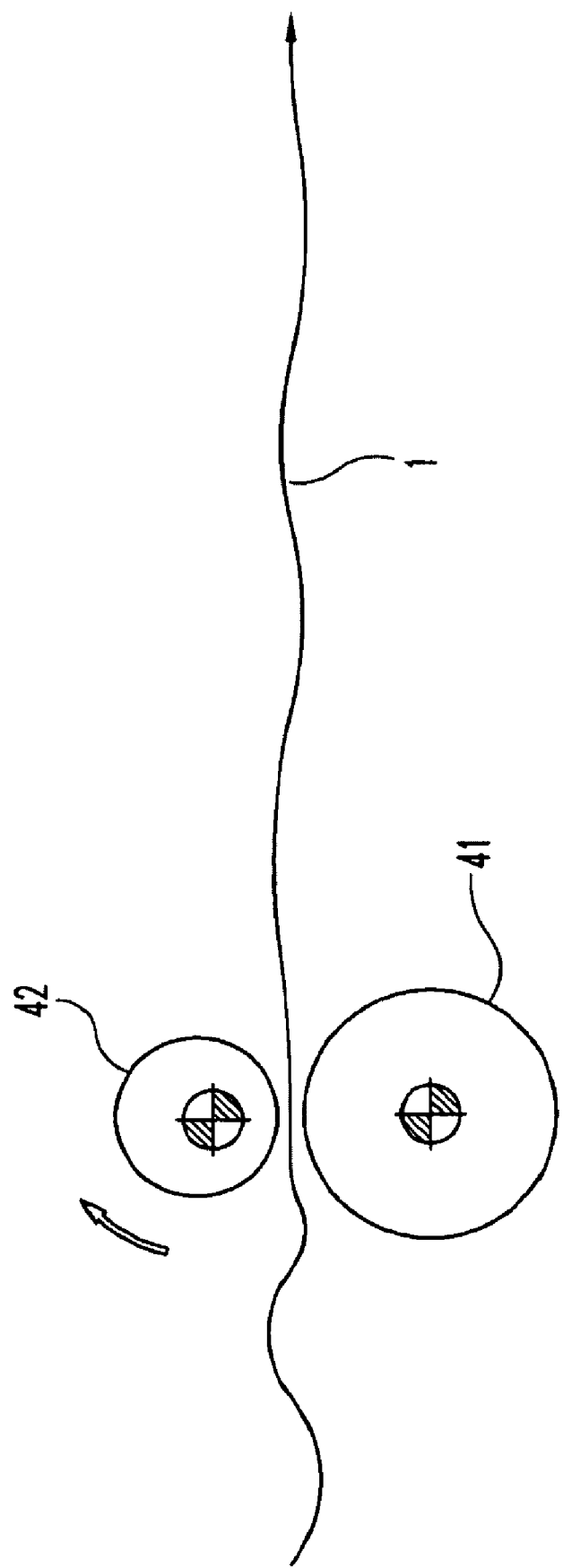
FIG. 15 illustrates an open position of the alternative detail of FIG. 14.

FIGS. 14 and 15 illustrate an alternative embodiment of a strip retaining mechanism placed closed to a cartridge opening 11 instead of the active door 35. This embodiment may be preferable in cases in which a strip 1 that is tight sealed is used so that the cartridge 10 itself and its opening 11 do not have to be closed in a sealed manner as provided by the active door 35. It comprises a round roll 41 and an eccentric roll 42, wherein the eccentric roll 42 can be driven, e.g. by a motor with a transmission or by a spring, wherein the spring may be released by a memory-shape-metal actuator, e.g. made of nitinol. In FIG. 14 the mechanism is shown in the closed position, wherein pulling of the strip 1 increases the clamping force. In FIG. 15 the mechanism is shown in the open position wherein the strip 1 can be pulled out of the cartridge 10.

The brake for stopping the strip 1 can be provided in two manners. The first option is a cartridge 10 without an active door 35, wherein an additional external brake for stopping the strip 1 is used. Another possibility would be an active door 35 as described in FIGS. 12 and 13, which serves both for closing the cartridge 10 and as a brake for stopping the strip 1.

FIGS. 16 to 25 illustrate a sequence of pulling out a first chamber 2 of a cartridge 10 comprising a lancet 21 according to FIG. 6, performing an actuation step of the lancet 21 with an actuation means 20 for taking a blood sample of a finger 45, further pulling out a second chamber 2 of the box 10 comprising a test element 44 and further pressing the test element 44 against the skin of the finger 45 for collecting the blood. In FIGS. 16 to 25 the strip 1 in the cartridge 10 is wound around a roll 46. The cartridge 10 comprises an active door 35.

Figure 16:
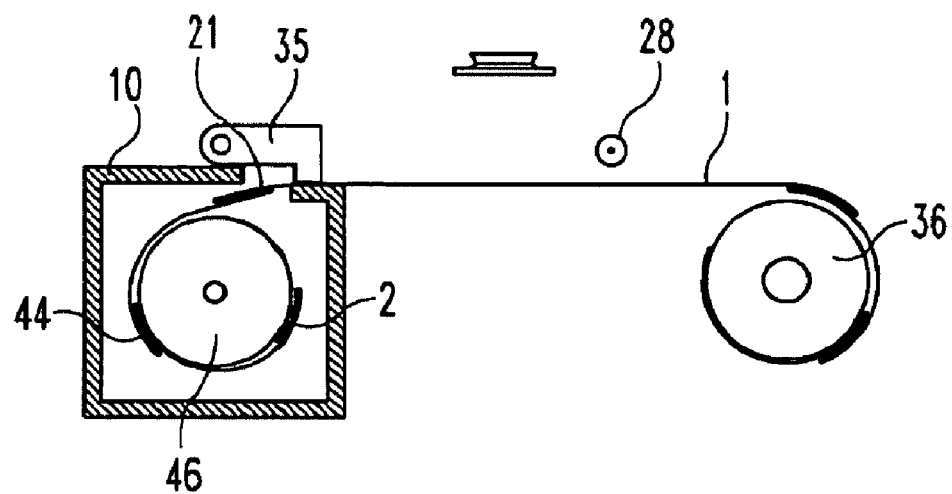
FIG. 16 illustrates a first step according to FIGS. 12 and 13.

In FIG. 16 the start position is shown. The active door 35 is closed and the strip 1 is kept under tension with a winding device 36.

Figure 17:
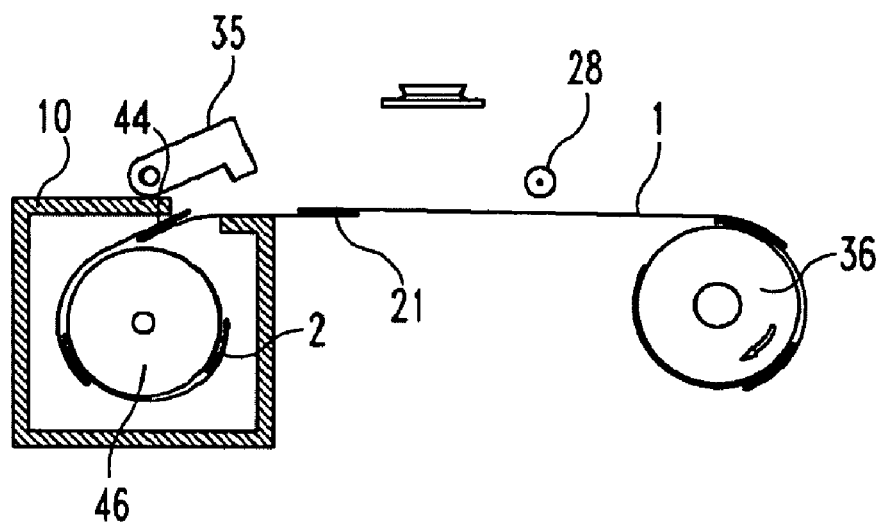
FIG. 17 illustrates a second step according to FIGS. 12 and 13.

In FIG. 17 a chamber 2 with a lancet 21 is pulled out of the cartridge 10 by winding the winding device 36 with the active door 35 open.

Figure 18:
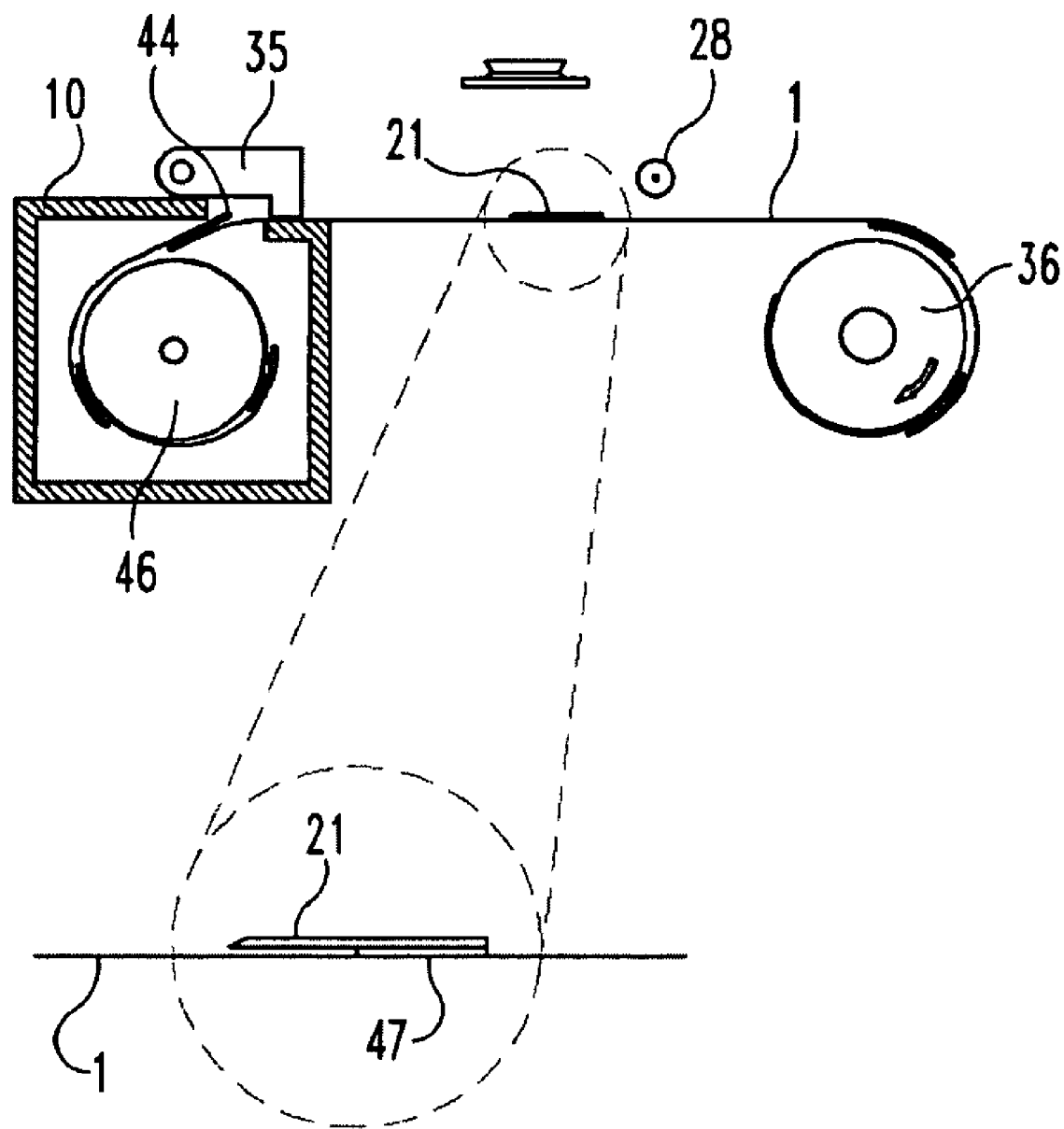
FIG. 18 illustrates a third step according to FIGS. 12 and 13.

In FIG. 18 the chamber 2 is unfolded for unwrapping of the lancet 21 out of the chamber 2. For this the active door 35 is closed and prevents a further movement of the strip 1 out of the cartridge 10. The winding device 36 continuous turning, wherein the chamber 2 comprising the lancet 21 is opened. The lancet 21 lies on the strip 1 and is fixed to the strip 1 with glue 47 at its back end.

Figure 19:
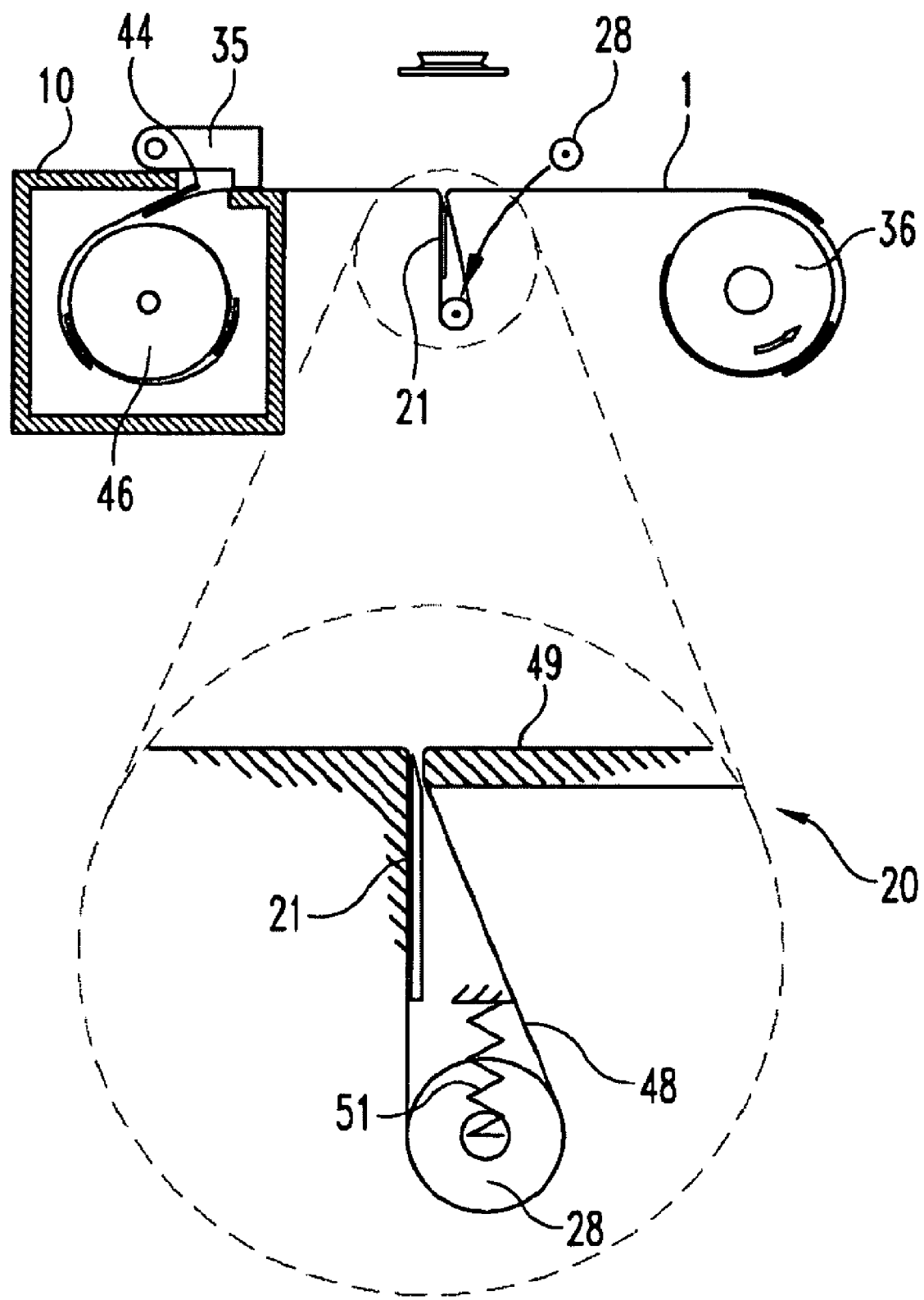
FIG. 19 illustrates a fourth step according to FIGS. 12 and 13.

In FIG. 19 the lancet 21 is raised from its direction parallel to the longitudinal direction of the strip 1 by about 90° by using an actuation means 20 comprising a roller 28. In this process, the flexibility of the strip 1 is used for raising the lancet 21, which is fixed with one end to the strip 1, for example by gluing. In order to have a sufficiently loose strip 1 for turning the direction of the lancet 21, the winding device 36 may be rewound. The actuation means 20 and the function of the roller 28 are described in more detail in FIGS. 26 and 27. It comprises a lever mechanism moving the roller 28 for folding the strip 1 in a loop 48 for moving the lancet 21. However, also other types of actuation means may be suitable.

Figure 20:
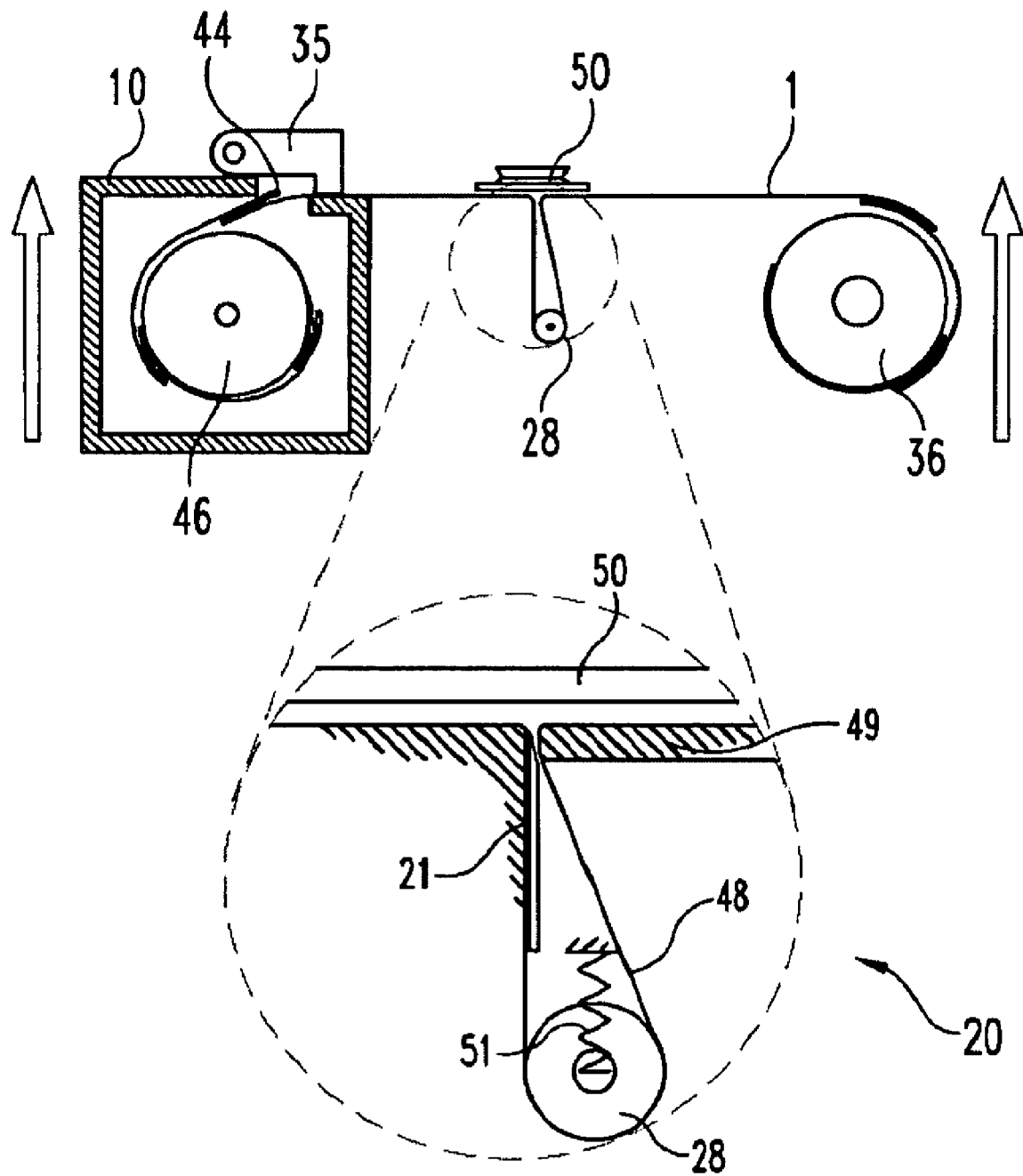
FIG. 20 illustrates a fifth step according to FIGS. 12 and 13.

In FIG. 20 a locating surface 49 is placed below the finger. In order to achieve this, the total actuation means 20 or the lever mechanism is moved into the direction of an opening 50 of the device, on which opening 50 the finger 45 to be pierced is or will be placed. The actuation means 20 is moved completely to the skin to be pierced, before the piercing step is performed with lancet 21. Upon this the strip 1 is moved until it has contact to the skin. However, the skin preferably has only contact to the strip 1, but not to other parts of the actuation means 20. This is advantageous with respect to sterility requirements and carry-over of materials into subsequent measurements.

The locating surface 49 onto which the skin is pressed via the strip 1 has the advantage that it provides that the emerging length of the lancet 21 upon performing the piercing into the skin is identical to the puncture depth of the lancet 21 into the skin pierced. In order to achieve this it is further advantageous if the skin is pressed against the locating surface 49.

Figure 21:
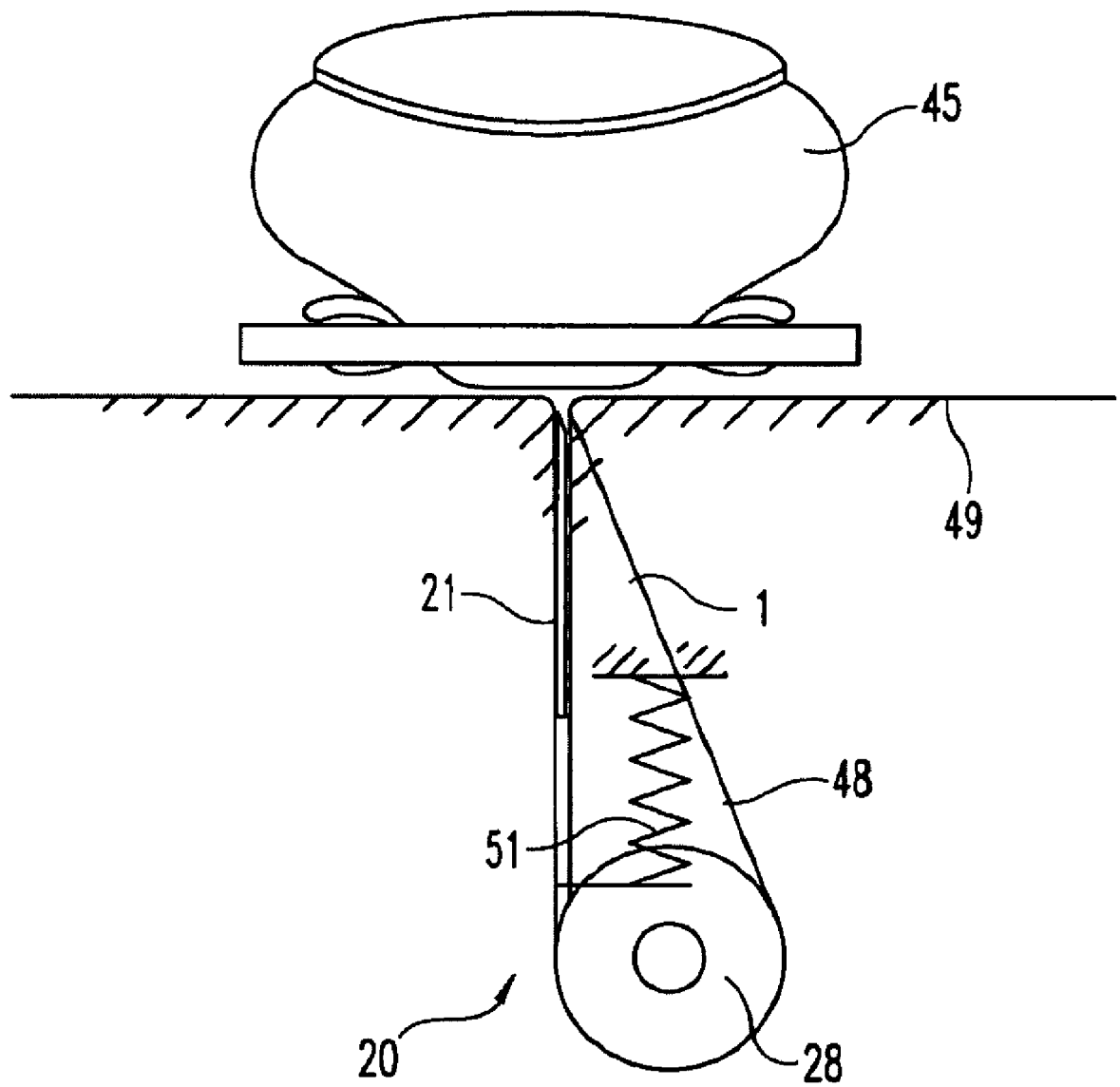
FIG. 21 illustrates a sixth step according to FIGS. 12 and 13.

In FIG. 21 the finger 45 is pressed against the opening 50.

Figure 22:
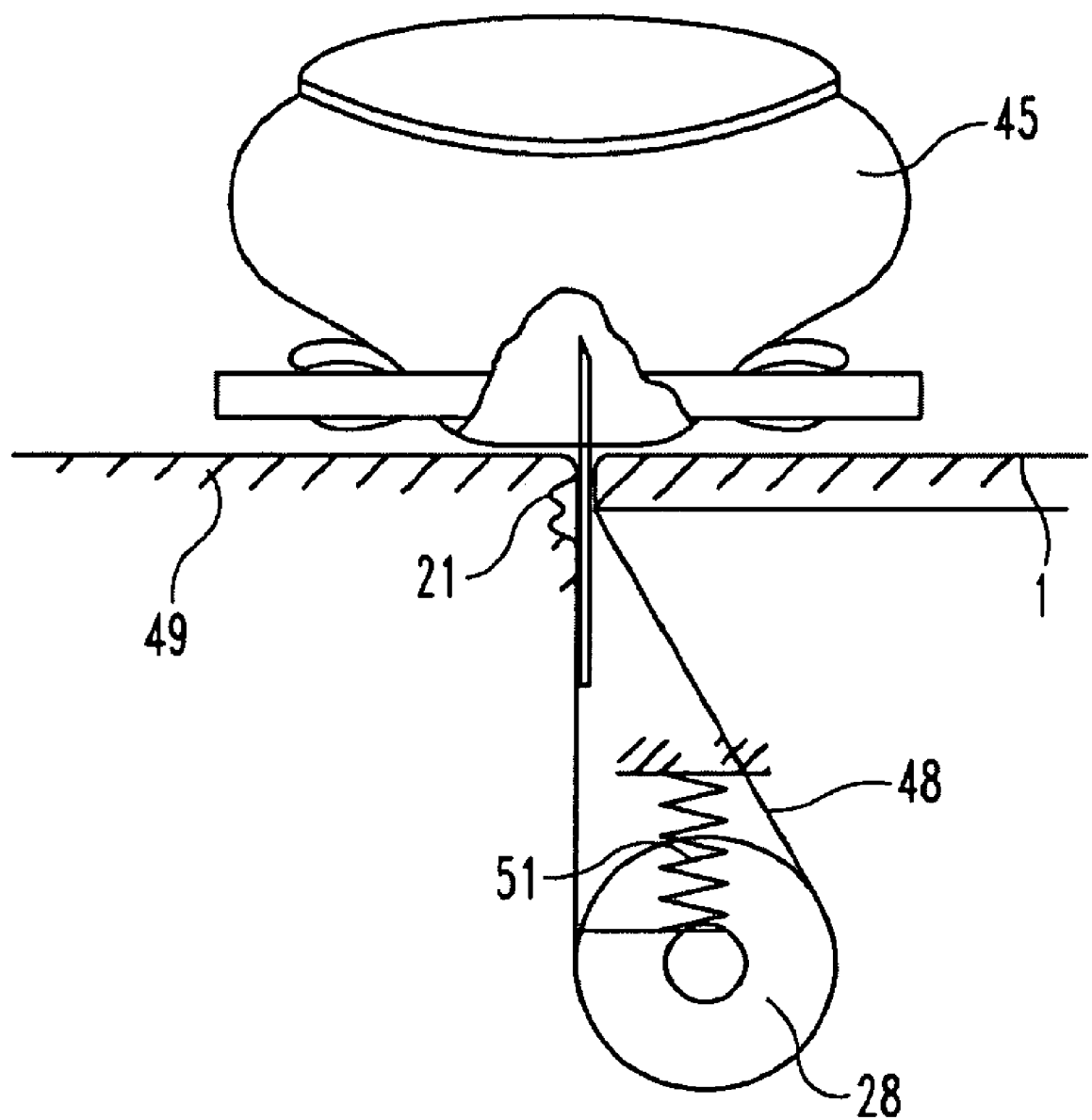
FIG. 22 illustrates a seventh step according to FIGS. 12 and 13.

In FIG. 22 skin piercing movement is performed of the lancet 21 into the finger 45. In order to enable that movement while maintaining the tensile stress in the strip 1, the roller 28 may be moved against the force of a spring 51.

Figure 23:
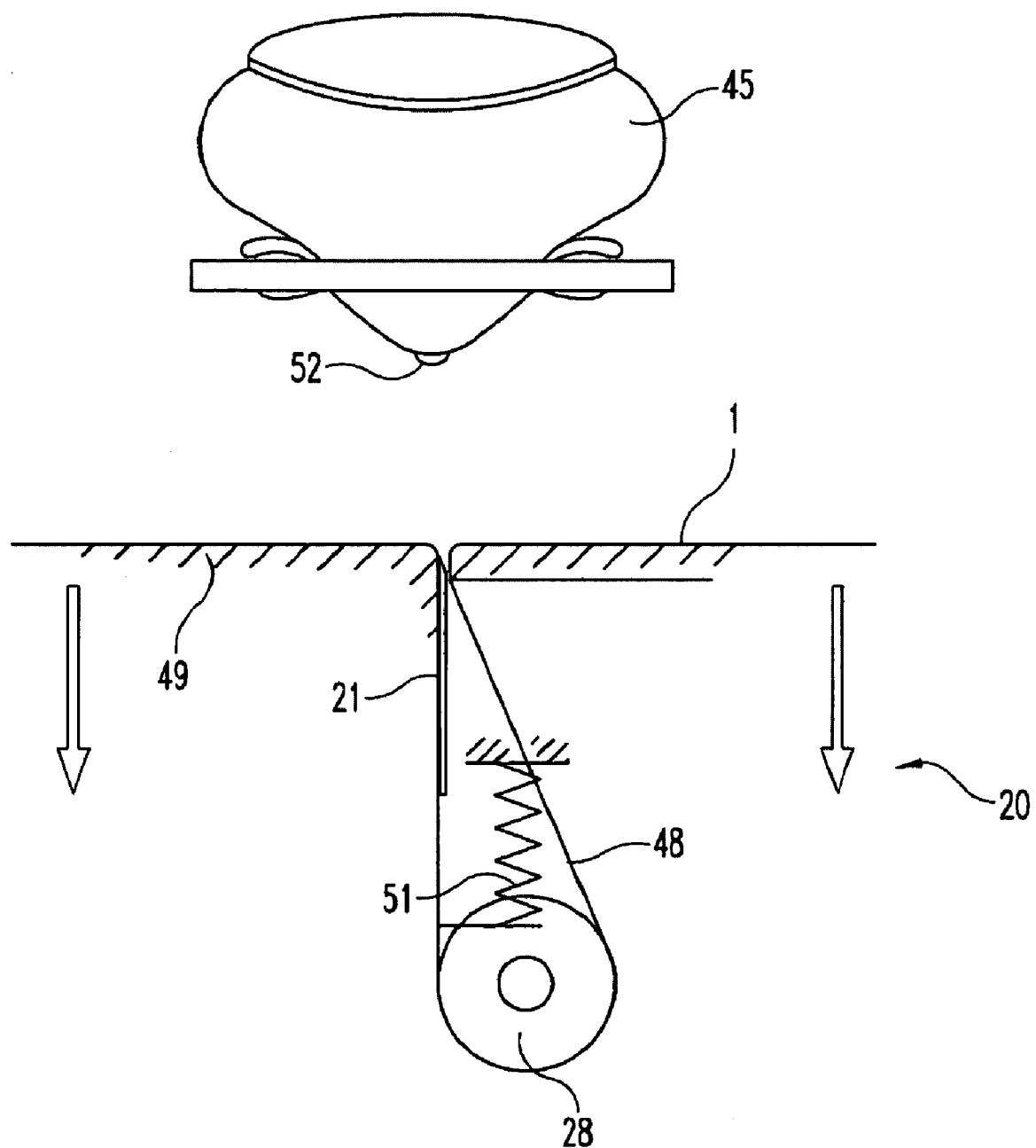
FIG. 23 illustrates an eighth step according to FIGS. 12 and 13.

In FIG. 23 the expression of blood 52 from the pierced skin is performed and the actuation means 20 and the lancet 21 are retracted from the finger 45.

Figure 24:
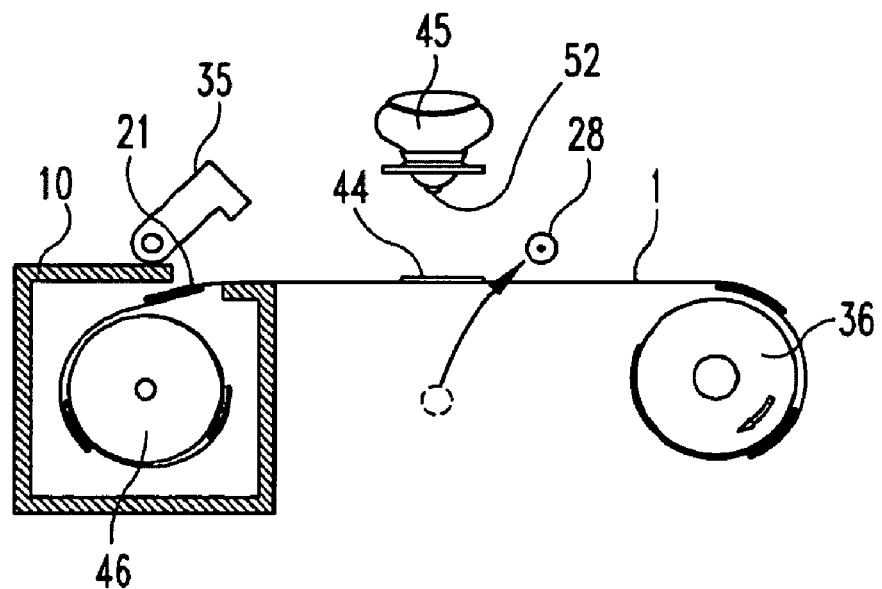
FIG. 24 illustrates a ninth step according to FIGS. 12 and 13.

In FIG. 24 a chemical test element 44 is fetched in a process similar to FIG. 17 by opening the active door 35 and pulling out the test element 44 from the cartridge 10 by winding the winding device 36. In case the test element 44 is disposed in a chamber 2 of strip 1, chamber 2 can be unfolded in a pulling step similar to that of FIG. 18 by closing the active door 35 and winding strip 1 with winding device 36. Finally, the test element 44 is located in a position under the blood 52 to be tested.

Figure 25:
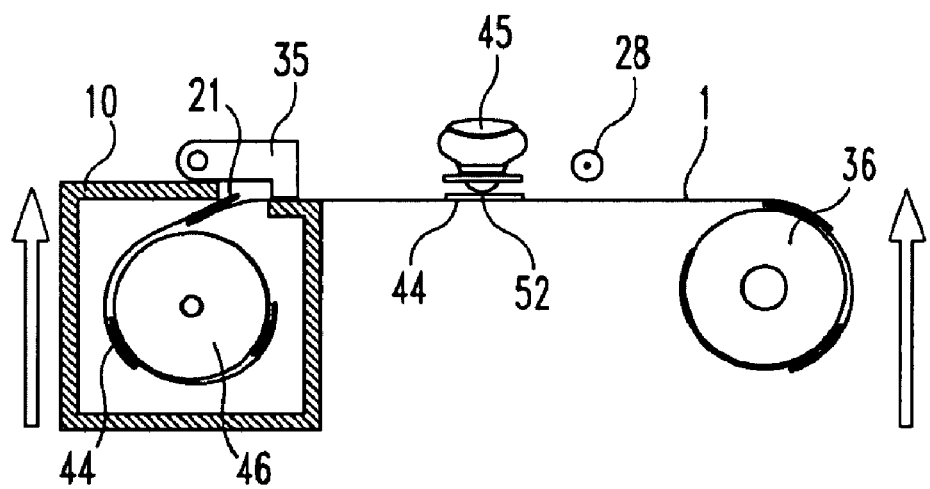
FIG. 25 illustrates a tenth step according to FIGS. 12 and 13.

In FIG. 25 the chemical test element 44 is brought into contact with the blood 52 expressed from the finger 45. In order to achieve this, the actuation means 20 is moved into the direction of the finger 45. After that step, the test element 44 can be forwarded by the strip 1 to an analyzing device, e.g. an optical glucose measurement device. The total process, starting with FIG. 16, can than be performed with the next lancet 21 and test element 44 of the strip 1.

Figure 26:
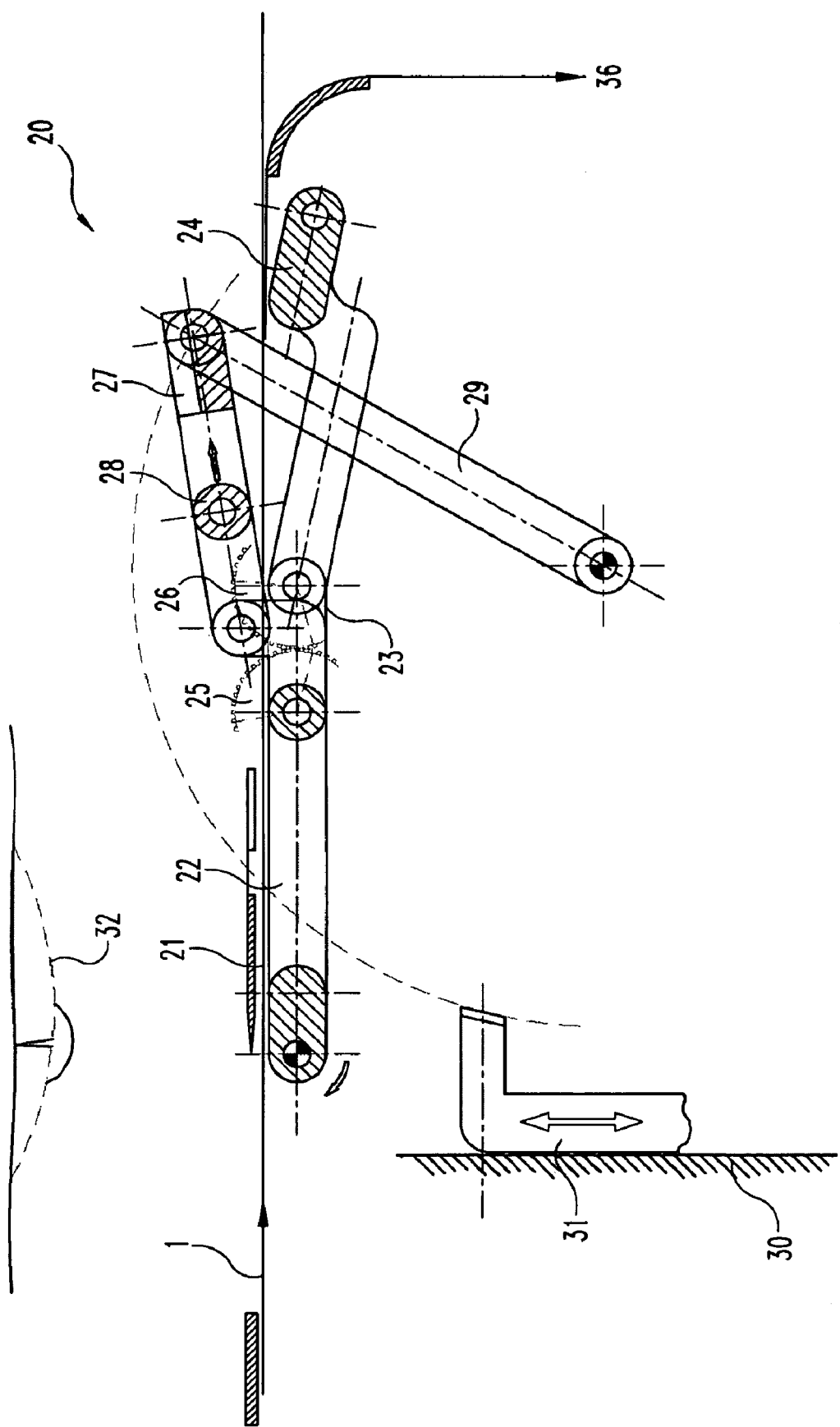
FIG. 26 shows a first actuation means in a first position.

FIG. 26 shows an actuation means 20 with a lever mechanism for lifting a medical device from the strip 1 of an open chamber 2. It is an actuation means for using a lancet 21 which is positioned on the strip 1 pulled out of the cartridge 10, wherein the chamber 2 has already been opened according to FIG. 6. The lancet 21 comprised in a chamber 2 is directed in the longitudinal direction of the strip, i.e. perpendicular to the direction of the breadthwise running fold lines 5. This is advantageous with respect to the further handling of the lancet 21 and the tape 1 as shown later in FIG. 27, because the tape 1 does not have to be displaced by the actuation means 20 in a direction perpendicular to the longitudinal direction of the tape 1 upon using the lancet 21 for taking a blood sample. Preferably the lancet 21 is fixed to the strip 1 with its back end opposed to the front end intended to puncture skin. However, the lancet 21 can also be placed in a direction across to the longitudinal extension of the tape 1 in case the actuation means 20 is adapted accordingly.

The lancet 21 is transported by the strip 1 into a defined position. It lies then on a first lever 22 which is connected by a short connecting rod 23 to a second lever 24. The movements of the two levers 22, 24 are synchronized by two segment gears 25 and 26. Lever 22 comprises a longitudinal slot on almost its entire length.

First lever 22 is slightly cranked at its end and is there pin-connected with a third lever 27. This third lever 27 supports a roller 28 which can be slid in the right direction. In addition the third lever 27 is connected to an oscillating link 29 that is in turn rotatably supported in a housing 30 of the actuation means 20. The first lever 22 or the oscillating link 29 is engaged with a swiveling drive unit (not shown) of the device. When the swiveling drive unit is active, the lever device is folded. During the folding movement the first lever 22, the oscillating link 29 and the connecting rod 23 together with the housing 30 form a four-link. The second lever 24 is forced to move due to the gear coupling of the segment gears 25 and 26. Auxiliary the right end of the second lever 24 can be led also in a groove in the magazine, wherein enough slack must be available so that no sticking occurs. During this folding movement, the tape guide roller 28 ensures that the tape 1 is pulled down.

In the last moment the lancet with its slot is threaded onto a cam 31, wherein the sharp grinding of the cam cuts the base material and engages into the slot in the lancet 21. The tape 1 now forms together with the ends of the first lever 22 and the second lever 24 a contact area that serves as a reference plane stabilizing the skin for performing the piercing with the lancet 21. For this purpose the entire mechanism is driven forward by a drive not shown until a reference area 32 of the skin is depressed with the necessary force.

Now the cam 31 drives the lancet 21 forward into the skin and moves it back again according to FIG. 27, i.e. the lever mechanism of the actuation means 20 is designed for performing a piercing movement with the lancet 21, wherein the lever mechanism is designed to turn the direction of the medical device by 90° compared to its starting position and the strip 1 according to FIG. 26. Upon movement of the lancet 21 by the cam 31, the roller 28 bounces into a position 33 and back again and as such guarantees that the piercing movement is not hindered. In addition, the tensile stress in the tape 1 that supports the lancet 21 provides that the lancet 21 maintains proper adjustment. Only the short tape section between the lancet 21 and the stationary hinge of first lever 22, onto which the skin presses, falls loosely during the piercing and must find enough place to make a way without interrupting the course.

The lancet 21 has a longitudinal slot 53 for its guiding on the cam 31. Due to the tensile stress of the strip 1, a straight guiding of the lancet 21 is achieved, without that an additional guiding is required at the front end of the lancet 21. The lancet 21 can be of any suitable shape, e.g. flat or round.

Two operation modes of the actuation means 20 are possible. In the first mode the lancet 21 is pierced only shortly into the skin and afterwards the total mechanics are immediately retracted again of the skin. Then the mechanics are unfolded again and a test element is provided from the stock, for example from another chamber on the packaging strip 1, and the test element is transported by the unfolded folding mechanics to the skin in order to take up blood.

According to a second operation mode, the test element already waits between the second lever 24 and the third lever 27, but still below the bottle neck between the first lever 22 and the second lever 24. The piercing movement in this case looks a little different. The lancet 21 is pierced and withdrawn up to a rest of 0.5 mm. Afterwards the complete mechanics moves very slowly away of the skin, wherein the lancet 21 takes up blood with a capillary channel which is open to the right.

After that the test element is pulled out of its waiting position a little up by the drive unit of the tape 1 and the folding mechanics is closed completely with some force, wherein the chemical layer is pressed against the open side of the capillary channel in the tip of the lancet 21. In this manner the blood is transferred from the lancet 21 to the test element. After that the folding mechanics is opened and the test field is transported to the evaluation optics.

An advantage of this mechanics is that all parts that project above the tape transport level in the opened state are so remote from the axis of the piercing movement that the tape 1 can be transported to a position directly under the milking cone.

In another embodiment no test element may be involved and the actuation means 20 may be only used for performing a piercing movement with the lancet 21 without providing a transport of the blood to a test element.

Figure 27:
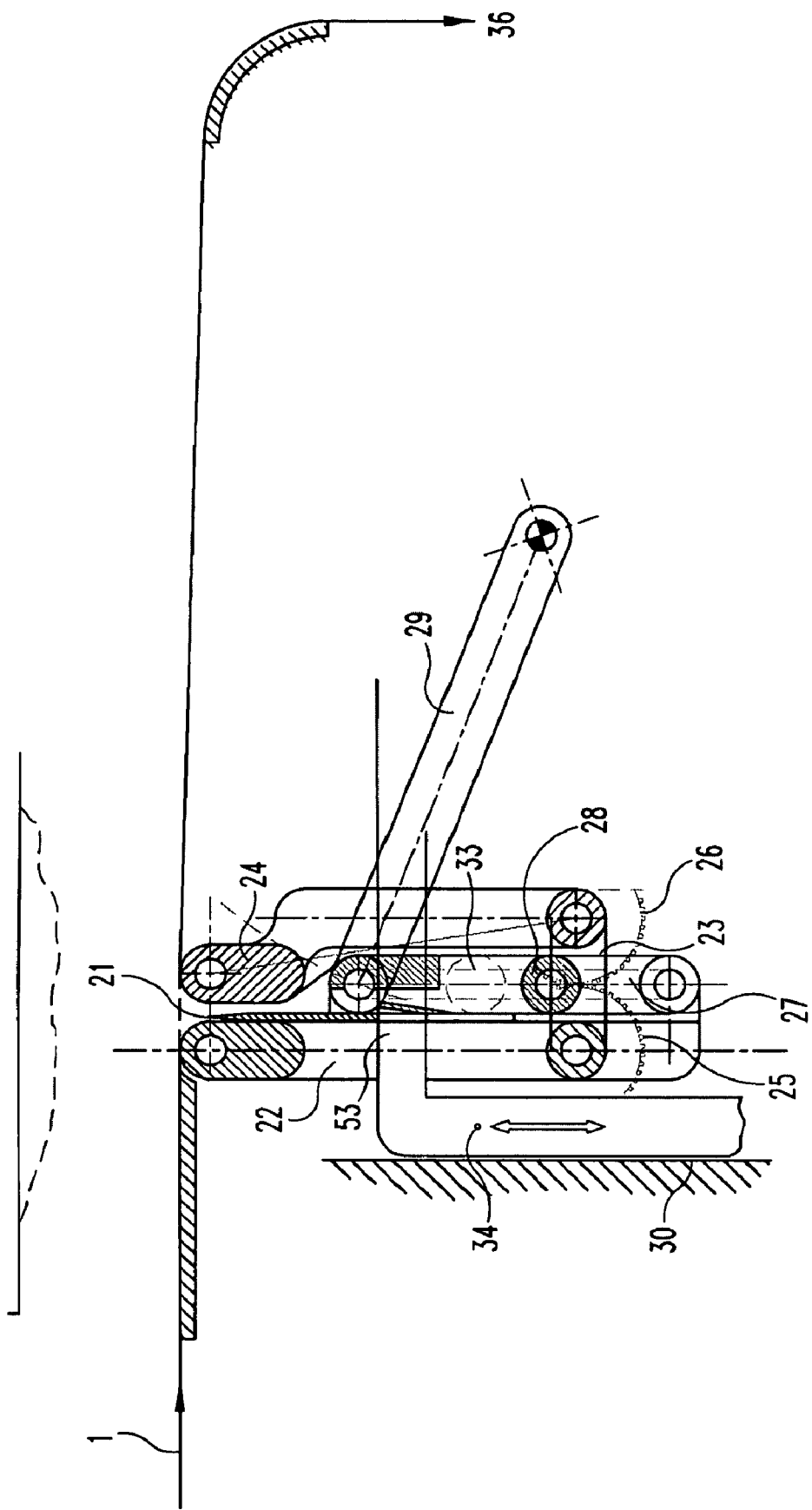
FIG. 27 shows the actuation means of FIG. 26 in a second position.

Although the actuation means 20 shown in FIGS. 26 and 27 can be preferably used in a packaging system according to the present invention, it can be also used in other medical apparatus for handling a medical device provided by a strip.

In general terms, an actuation means as shown in FIGS. 16 to 27 has the following advantage features. The actuation means 20 comprising a lever mechanism for actuating disposable medical devices of a packaging strip 1 that is elongated in a longitudinal direction, wherein medical devices are placed on the packaging strip 1 parallel to the elongated direction of the strip 1 before they are actuated by the actuation means 20, in particular an actuation means 20 as described in this application to be used in a packaging system with folded strips 1, is characterized in that the medical devices are fixed with one end to the packaging strip 1, for example by an adhesive, the lever mechanism is constructed to move the medical devices together with the section of the strip 1 to which they are fixed by moving the strip 1, and the strip 1 is folded by the actuation means 20 in a loop 48 for moving the medical device.

According to an additional preferable embodiment the medical device is a lancet 21 and the lever mechanism is designed for performing a piercing movement with the lancet 21.

According to another additional preferable embodiment the lever mechanism is designed to turn the direction of the medical device by about 90° into a buckleproof position of the strip 1. For this purpose it is preferable when the lever mechanism comprises a roller 28 over which the strip 1 is guided with tension in its longitudinal direction for enabling turning the direction of the medical device without exerting a peeling load onto the strip 1 or onto the fixing of the medical device to the strip 1 and without bending the medical device. Another additional preferable feature may be that the actuation means 20 comprises a spring storage strip device 54 for paying out the packaging strip 1 with tension in its longitudinal direction for enabling turning the direction of the medical device without having to turn back a reel 55 of a winding device 36 onto which the strip 1 is wound.

As shown in the figures it is preferable when the lever mechanism comprises a locating surface 49 providing a reference surface 32 for placing the actuation means 20 in a defined distance with respect to skin to be pierced by the actuation means 20. In this embodiment it may additionally be preferred that the strip 1 is placed between the locating surface 49 and the skin to be pierced by the actuation means 20.

According to an other preferable embodiment of the actuation means 20 it comprises a moving mechanism by which the actuation means 20 can be moved to skin to be pierced with a lancet 21 of the packaging strip 1 until the packaging strip 1 clings to the skin to be pierced before a piercing movement with the lancet 21 is performed.

Figure 28:
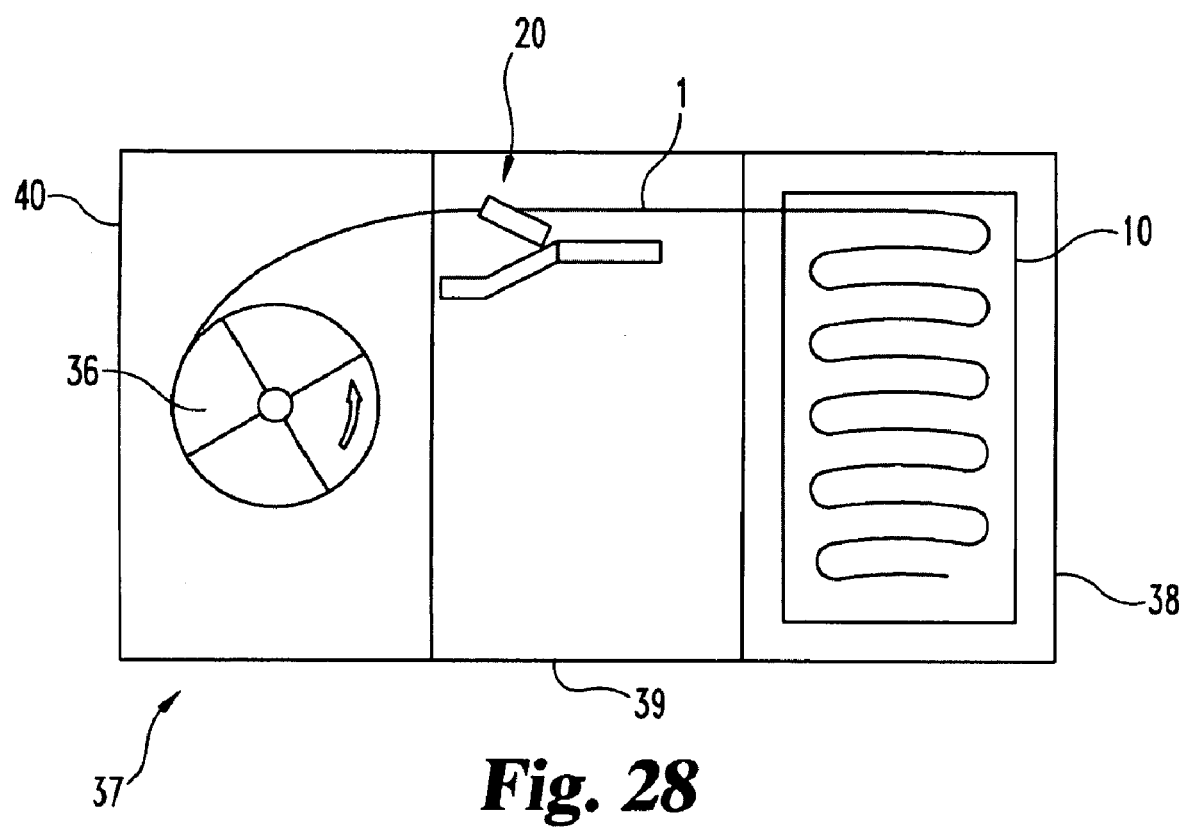
FIG. 28 shows a packing system with three modules.

FIG. 28 shows a packaging system comprising a cartridge 37 that includes a fresh module 38 comprising unused medical devices in a packaging strip 1, e.g. a cartridge 10 as shown in FIG. 6, an actuation module 39 comprising an actuation means for actuating a medical device pulled out of the fresh module, e.g. an actuation means 34 as described in FIGS. 26 to 27, and a waste module 40 for taking up used medical devices and the corresponding part of the strip, the waste module 40 also comprising the winding device 36 for transporting the strip 1 from the fresh module 38 via the actuation module 39 to the waste module 40. The winding device 36 may be secured against rewinding, e.g. by comprising a one-way clutch.

The cartridge 37 can be easily inserted into a corresponding analysis apparatus, e.g. a blood glucose meter used for piercing skin and performing a blood glucose measurement. The medical devices required, e.g. lancets 21 and/or analysis means for receiving a blood sample, are comprised in the chambers 2 of the strip in the fresh module 38. They are transported one after another to the actuation module 39 for use in the analysis apparatus and disposed in the waste module 40. The total length of the strip 1 may be in the order of 5 cm. When all medical devices included in its chambers 2 are used up the complete cartridge 37 is taken out from the analysis apparatus and discharged.

Figure 29:
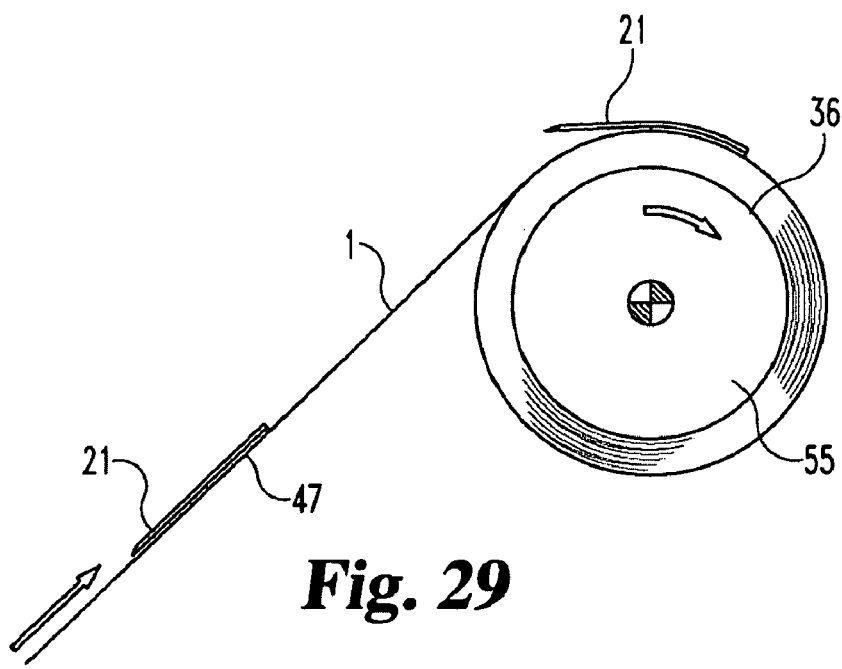
FIG. 29 shows the winding device according to FIG. 28.
Figure 30:
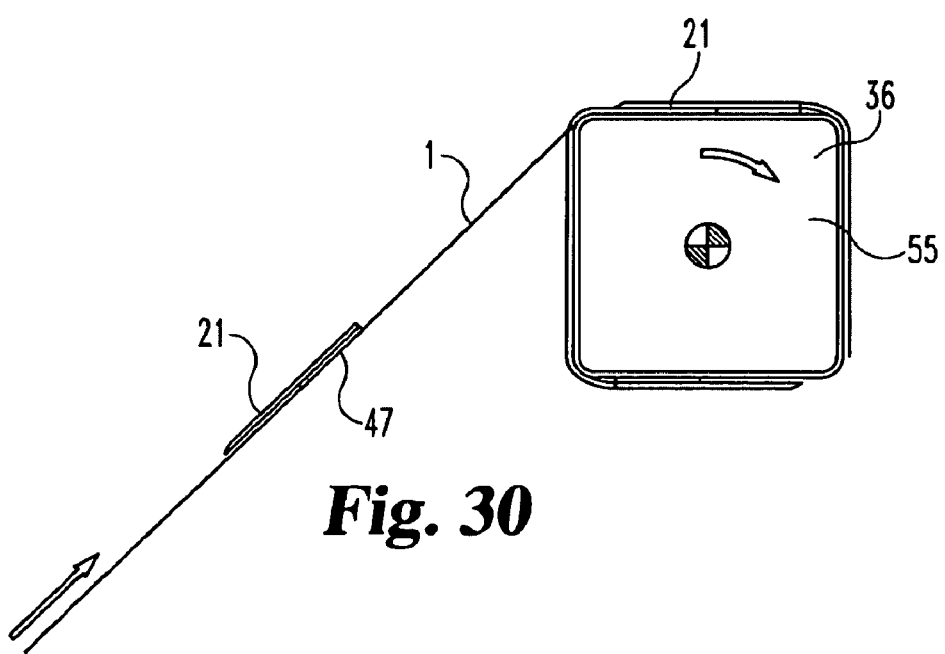
FIG. 30 shows an alternative winding device.

FIG. 29 shows the winding device 36 with the reel 55 for winding the strip 1 with used lancets 21 and optionally also used test elements 44. However, the winding device 36, i.e. the reel 55, does not necessarily have to be round, but it also can be polygonal in shape. An example of such a polygonal embodiment of a reel 55 is shown in FIG. 30. Of course, also the fresh, unused medical disposables do not have necessarily to be folded in a stack as shown in cartridge 10 of FIG. 6 or wound on a roll 46 as shown in FIG. 16, but can also be wound on a polygonal roll. In embodiments, in which the roll is round, it is preferred when the diameter of the roll is large that the lancets 21 lying in a longitudinal direction of the strip 1 are not bent too much on the roll. In polygonal embodiments the diameter of the reel 55 has to be adjusted to the sequence distance of the disposables on the strip 1.

Figure 31:
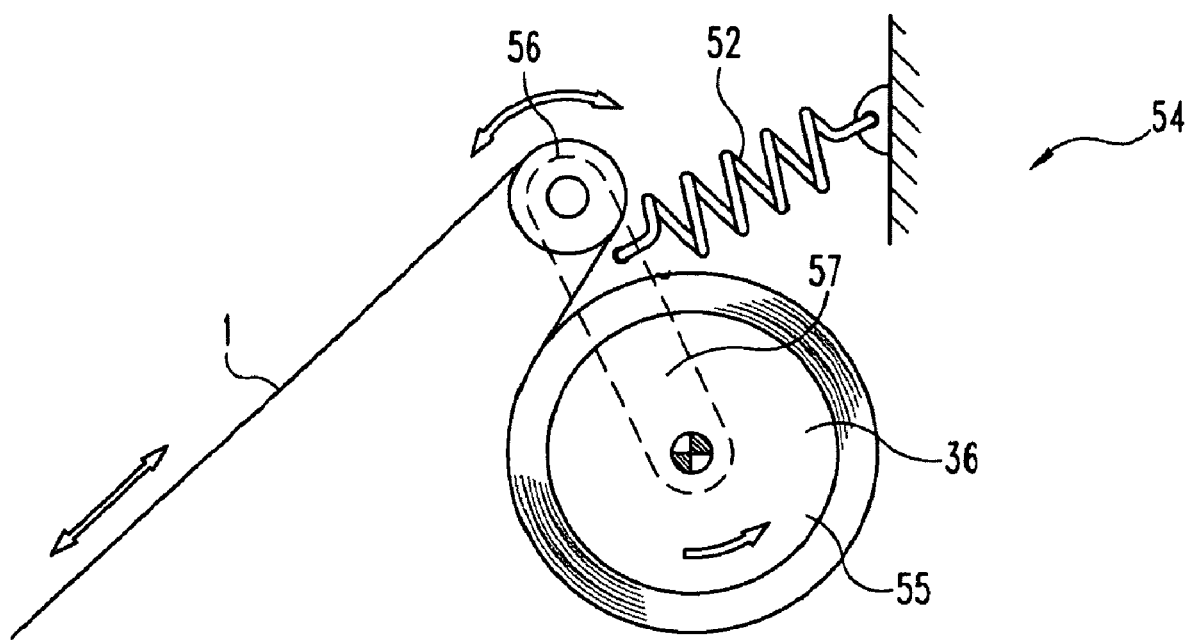
FIG. 31 shows another alternative winding device.

FIG. 31 shows an alternative embodiment of a winding device 36. It is a spring storage strip device 54 for paying out the packaging strip 1 with tension in its longitudinal direction for enabling turning the direction of a medical device placed on the strip 1 without having to turn back the reel 55 of the winding device 36 onto which the strip 1 is wound. For this purpose the strip storage spring device 54 comprises a roller 56 on a lever 57 which is held under tension with a spring 58. The device 54 enables to pull out a little strip 1 from the winding device 36 without turning back the reel 55. This embodiment is advantageous with respect to hygiene aspects because the used lancets 21 are kept wound on the reel 55. A corresponding spring storage strip device can also be provided on the fresh, unused side of the strip 1.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

LIST OF REFERENCE NUMERALS 1 packaging strip
2 chambers
3 section
4 section
5 fold lines
6 adhesive frame
7 adhesive patch
8 disposable
9 section
10 cartridge
11 cartridge opening
12 sidewall
13 sidewall
14 sidewall
15 service loop
16 compression spring
20 actuation means
21 lancet
22 first lever
23 connecting rod
24 second lever
25 segment gear
26 segment gear
27 third lever
28 roller (tape guide roller)
29 oscillating link
30 housing
31 cam
32 reference area
33 position
34 actuation means
35 active door
36 winding device
37 cartridge
38 fresh module
39 actuation module 40 waste module
41 round roll
42 eccentric roll
43 sidewall
44 test element
45 finger
46 roll
47 glue
48 loop
49 locating surface
50 opening
51 spring
52 blood
53 slot
54 strip storage spring device
55 reel
56 roll
57 lever
58 spring

The invention claimed is:

1. A packaging system comprising disposable medical devices and a packaging strip comprising a plurality of chambers containing the disposable medical devices,
the strip being folded along breadthwise running fold lines to form a series of loops, each loop comprising opposing sections,
the opposing sections of at least some of the loops being sealed to each other thus forming chambers between said sections;
wherein the strip comprises in its longitudinal direction an alternating sequence of chambers comprising two types of medical devices; and
wherein the alternating sequence of chambers comprising a lancet in one chamber and comprising a test element in a subsequent chamber.

2. Packaging system according to claim 1, wherein the sections of the strip are sealed by means of an adhesive.

3. Packaging system according to claim 2, wherein the adhesive allows the chambers to be opened by peeling the opposing sections apart.

4. Packaging system according to claim 1, wherein the strip is made of release paper.

5. Packaging system according to claim 1, wherein a section of the strip forming a chamber bottom is arranged on top of a section of the strip forming a chamber top of an adjacent chamber.

6. Packaging system according to claim 5, wherein loops forming adjacent chambers of the strip are fixed to each other by a releasable adhesive, preferably an adhesive patch, placed between the section forming the chamber bottom of a first chamber and the section forming the chamber top of a second chamber.

7. Packaging system according to claim 1, wherein the chambers of the strip comprise a frame forming sidewalls of the chambers.

8. Packaging system according to claim 1, wherein the chambers of the strip are arranged on top of each other.

9. Packaging system according to claim 1, wherein the loops of the strip are arranged and sealed in such a way that when the strip is subject to a tensile stress, created by pulling at an end of the strip wherein the other end is held fixed, causes the loops to unfold and the chambers to open one after the other.

10. Packaging system according to claim 9, comprising a holding means for holding the strip against a pulling direction in order to assist opening a chamber of the strip.

11. Packaging system according to claim 1, wherein the strip comprises service loops that are formed between succeeding chambers in order to ensure that medical devices comprised in the chambers are located on the same side of the strip.

12. Packaging system according to claim 1, wherein the distance between subsequent chambers of the strip in the unfolded position of the strip is in the range of 3 cm to 20 cm, preferably in the range of 5 cm to 10 cm.

13. Packaging system according to claim 1, wherein each of the chambers of the strip contains a desiccant in addition to the disposable medical device.

14. Packaging system according to claim 1, wherein the lancet comprised in a chamber is directed in the longitudinal direction of the strip.

15. Packaging system according to claim 1, wherein the lancet is fixed to the strip with its back end opposed to the front end intended to puncture skin.

16. Packaging system according to claim 1, wherein each of the medical devices are constructed as an integrated device comprising the lancet and means for receiving a sample of a body fluid from a puncture wound created by piercing with the lancet.

17. A cartridge containing the packaging system according to claim 1, the cartridge having a slot-shaped opening for pulling an end of the strip out.

18. Cartridge according to claim 17, wherein the end of the strip protrudes through the opening.

19. Cartridge according to claim 17, comprising a holding means for holding the strip against a pulling direction in order to assist opening a chamber of the strip.

20. Cartridge according to claim 19, wherein the slot-shaped opening is constructed as an active door and provides a holding means.

21. A packaging system comprising disposable medical devices and a packaging strip comprising a plurality of chambers containing the disposable medical devices,
the strip being folded along breadthwise running fold lines to form a series of loops, each loop comprising opposing sections,
the opposing sections of at least some of the loops being sealed to each other thus forming chambers between said sections; and
an actuation means with a lever mechanism for actuating a medical device of an open chamber of the strip.

22. A packaging system comprising disposable medical devices and a packaging strip comprising a plurality of chambers containing the disposable medical devices,
the strip being folded along breadthwise running fold lines to form a series of loops, each loop comprising opposing sections,
the opposing sections of at least some of the loops being sealed to each other thus forming chambers between said sections; and
a cartridge that includes a fresh module comprising unused medical devices in the packaging strip, an actuation module comprising an actuation means, and a waste module for taking up used medical devices and the corresponding part of the strip.

23. Packaging system according to claim 22, wherein the actuation means includes a lever mechanism for actuating a medical device of an open chamber of the strip.

24. Packaging system according to claim 22 in which the actuation means includes a lever mechanism for actuating the disposable medical devices of the packaging strip that is elongated in a longitudinal direction, wherein the medical devices are placed on the packaging strip parallel to the elongated direction of the strip before they are actuated by the actuation means,
  wherein
    the medical devices are fixed with one end to the packaging strip, for example by an adhesive,
    the lever mechanism is constructed to move the medical devices together with the section of the strip to which they are fixed by moving the strip, and
    the strip is folded by the actuation means in a loop for moving the medical device.

* * * * *